United States Patent
Hassibi et al.

(10) Patent No.: US 9,223,929 B2
(45) Date of Patent: Dec. 29, 2015

(54) METHOD AND APPARATUS FOR DETECTION, IDENTIFICATION AND QUANTIFICATION OF SINGLE-AND MULTI-ANALYTES IN AFFINITY-BASED SENSOR ARRAYS

(75) Inventors: Babak Hassibi, San Marino, CA (US);
Haris Vikalo, Pasadena, CA (US);
Arjang Hassibi, Palo Alto, CA (US)

(73) Assignee: The California Institute of Technology, Pasadena, CA (US)

( * ) Notice: Subject to any disclaimer, the term of this patent is extended or adjusted under 35 U.S.C. 154(b) by 1588 days.

(21) Appl. No.: 11/376,398

(22) Filed: Mar. 14, 2006

(65) Prior Publication Data
US 2007/0099198 A1 May 3, 2007

Related U.S. Application Data

(60) Provisional application No. 60/661,396, filed on Mar. 14, 2005.

(51) Int. Cl.
| | |
|---|---|
| G06F 7/60 | (2006.01) |
| G01N 33/48 | (2006.01) |
| G01N 31/00 | (2006.01) |
| G01N 33/50 | (2006.01) |
| G06F 19/20 | (2011.01) |
| G06F 19/12 | (2011.01) |
| G06F 19/24 | (2011.01) |
| G06F 19/22 | (2011.01) |

(52) U.S. Cl.
CPC ............... *G06F 19/20* (2013.01); *G06F 19/12* (2013.01); *G06F 19/22* (2013.01); *G06F 19/24* (2013.01)

(58) Field of Classification Search
None
See application file for complete search history.

(56) References Cited

U.S. PATENT DOCUMENTS

| 6,169,981 B1 | 1/2001 | Werbos |
| 6,516,276 B1 * | 2/2003 | Ghandour et al. .............. 702/27 |
| 2003/0130973 A1 | 7/2003 | Sumner et al. |
| 2003/0225718 A1* | 12/2003 | Shmulevich et al. ........... 706/46 |
| 2006/0123516 A1* | 6/2006 | Ronen et al. .................. 800/289 |

FOREIGN PATENT DOCUMENTS

| WO | WO 02099397 A2 * | 12/2002 |
| WO | WO 2004/011144 A2 * | 2/2004 |

OTHER PUBLICATIONS

Khabzaoui et al. A multicriteria genetic algorithm to analyze DNA microarray data. Proceedings of the 2004 congress on evolutionary computation. Jun. 2004. pp. 1874-1881.*
Cronin et al. Human Mutation, vol. 7, 1996, pp. 244-255.*
Yuen et al. Nucleic Acids Research, 2002, vol. 30, p. e48.*
Zhang Z. Noisy Data with Outliers, one page, 1996. Obtained online on Feb. 9, 2013.*
Stochastic Matrix, one page, 2013. Wolfram MathWorld. Obtained online on May 29, 2013.*

(Continued)

*Primary Examiner* — Russell S Negin
(74) *Attorney, Agent, or Firm* — Joseph R. Baker, Jr.; Gavrilovich, Dodd & Lindsey LLP

(57) ABSTRACT

The disclosure provides methods, device, and systems for analyzing biological array data. In particular, the disclosure provides methods and computer implemented techniques for reducing interference in microarray data, and exploiting it to obtain more accurate readouts.

14 Claims, 15 Drawing Sheets

(56) References Cited

OTHER PUBLICATIONS

Vikalo et al. A statistical model for microarrays, optimal estimation algorithms, and limits of performance. IEEE Transactions on Signal Processing, vol. 54, Jun. 2006, pp. 2444-2455.*

Vikalo et al. Optimal estimation of gene expression levels in microarrays. Presented at the IEEE Int. Workshop Genomic Signal Processing Statistics, Newport, RI, May 22-24, 2005.*

Proof of publication date of [Vikalo et al. Optimal estimation of gene expression in microarrays.] as Mar. 5, 2005, one page, acquired from USPTO Library on Jun. 13, 2014.*

Brodsky, Leonid, et al. "Identification and handling of artifactual gene expression profiled emerging in mircoarray hybridization experiments" Nucleic Acids Research. 2004. pp. 1-12. vol. 32, No. 4. Oxford University Press.

Hassibi, Arjang, et al. "Biological shot-noise and quantum-limited signal-to-noise ration in affinity-based biosensors" J. of Applied Physics. 2005. pp. 084701-01-084701-10. vol. 97. American Institute of Physics.

Hassibi, Arjang, et al. "Effects of Scaling on the SNR and Speed Biosensors" Proceedings of the 26th Annual Int. Conference of the IEEE EMBS. Sep. 1-5, 2004. San Francisco, CA USA.

Held, G.A., et al. "Modeling of DNA microarray data by using physical properties of hybridization" PNAS. Jun. 24, 2003. pp. 7575-7580.

Held, G. A., et al. "Relationship between gene expression and observed intensities in DNA microarrays—a modeling study" Nucleic Acids Research 2006. pp. 1-15. vol. 34, No. 9. Oxford University Press.

Reverter, A., et al. "A Rapid method for computationally inferring transcriptome coverage and microarray sensitivity" Bioformatics. 2005. pp. 80-89. vol. 21, No. 1. Oxford University Press.

Tu, Y., et al. "Quantitive noise analysis for gene expression microarray experiments" PNAS. Oct. 2002. pp. 14031-14036. vol. 99, No. 22.

* cited by examiner

US 9,223,929 B2

METHOD AND APPARATUS FOR DETECTION, IDENTIFICATION AND QUANTIFICATION OF SINGLE-AND MULTI-ANALYTES IN AFFINITY-BASED SENSOR ARRAYS

CROSS-REFERENCE TO RELATED APPLICATIONS

This application claims priority under 35 U.S.C. §119 to U.S. Provisional Application Ser. No. 60/661,396, filed Mar. 14, 2005, the disclosure of which is incorporated herein by reference.

FIELD OF THE INVENTION

The invention relates to the field of analyte detection. More specifically, the invention relates to methods, compositions and apparatus for analyte detection, identification and/or quantification in array-based sensors.

BACKGROUND

In the past decade, high-throughput assay technologies have gained attention in the genomic and proteomic research community. DNA microarrays, which in principle is a widely used affinity-based biosensor system, have attracted much interest due to the large scale, parallel nature of the experiments and the richness of the information obtained. This stands in contrast to traditional biosensing techniques capable of analyzing only a small number of analytes at any particular time.

DNA microarrays are primarily used to measure gene expression levels by affinity-based principle. Changes in DNA expression levels are often an indication of diseases; thus, DNA microarray experiments provide valuable insight into genetic changes in cells. Such insight is useful in detecting and treating disease and disorders as well as optimizing cellular differentiation, culture conditions and protein production. The generation of such valuable information is useful in the development of molecular diagnostics and personalized medicine.

Accordingly, optimal estimations of analytes, such as gene expression profiling, is important for proper diagnosis and research.

SUMMARY OF THE INVENTION

The invention provides a method of processing affinity-based array data. The method includes determining a theoretical estimate and/or an empirical estimate of a probe and a target interaction in an array; generating a probability matrix based on the theoretical and/or empirical estimates; obtaining data comprising a plurality of measured signals from an array; and applying an optimization algorithm that exploits non-specific interactions.

In another aspect, the invention provides a computer implemented method described herein.

The invention also provides an automated system of quantifying microarray data comprising a computer implemented method of the invention.

The invention further provides a computer program, residing on a computer-readable medium, comprising instructions for causing a computer to determine a theoretical estimate and/or an empirical estimate of a probe and a target interaction in an array; generate a probability matrix based the theoretical and/or the empirical estimates; apply experimental data to the probability matrix; apply an optimization algorithm that exploits non-specific interactions; and output specific binding data that depicts substantially accurate specific binding.

In yet a further aspect, the invention provides an apparatus comprising a computer-readable storage medium tangibly embodying program instructions for quantifying microarray image data, the instructions operable for causing the apparatus to determine a theoretical estimate and/or an empirical estimate of a probe and a target interaction in an array; generate a probability matrix based the theoretical and/or the empirical estimates; apply experimental data to the probability matrix; apply an optimization algorithm that exploits non-specific interactions; and output specific binding data that depicts substantially accurate specific binding from the microarray image data.

DETAILED DESCRIPTION

Figure 1A:
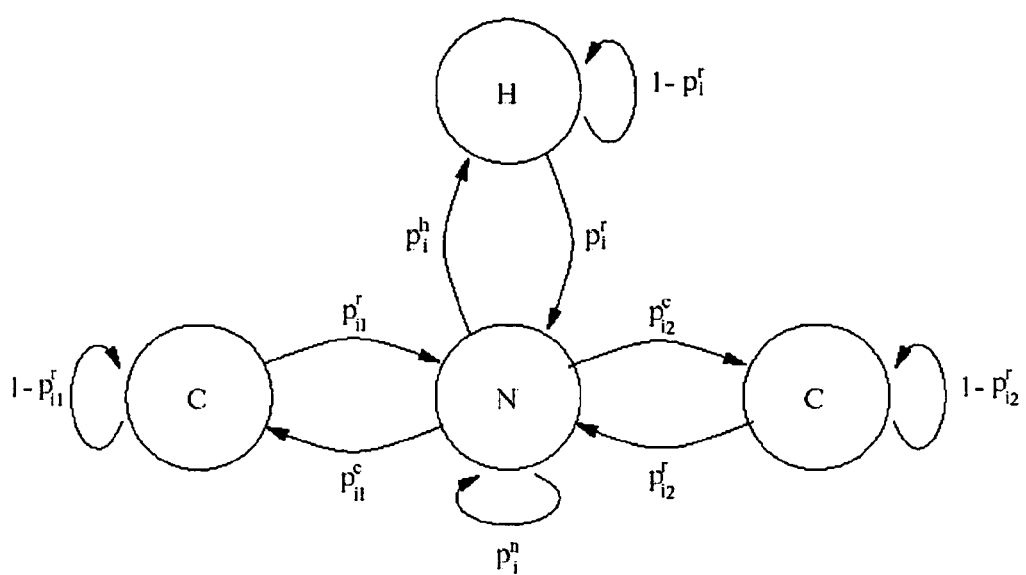
FIG. 1A-F show a general model and process of the invention. (A) is a Markov chain modeling states of a target molecule on a microarray with one specific and k=2 non-specific binding sites for illustration. The hybridized state is denoted by 'H', cross-hybridized states are denoted by 'C', and the unbound state is denoted by 'N'. (B) shows a typical process and depiction of signal intensity. (C) Shows an array image of a typical measurement. (D) shows a process of the invention and a depiction of signal intensity using the methods of the invention. (E) shows and ideal detection measurement. (F) shows a representative algorithm of the invention.
Figure 1B:
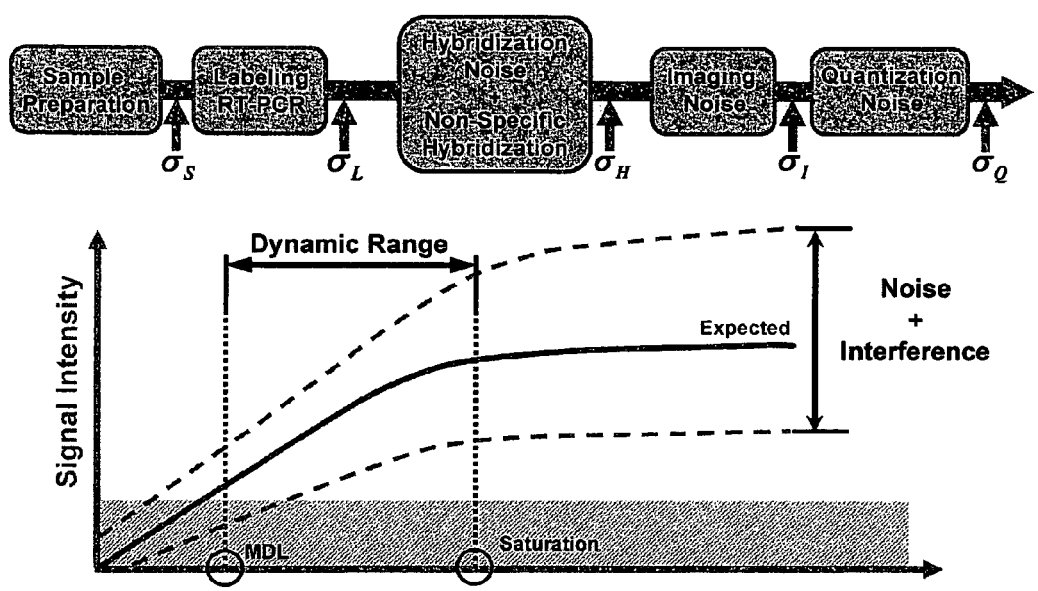
Figure 1C:
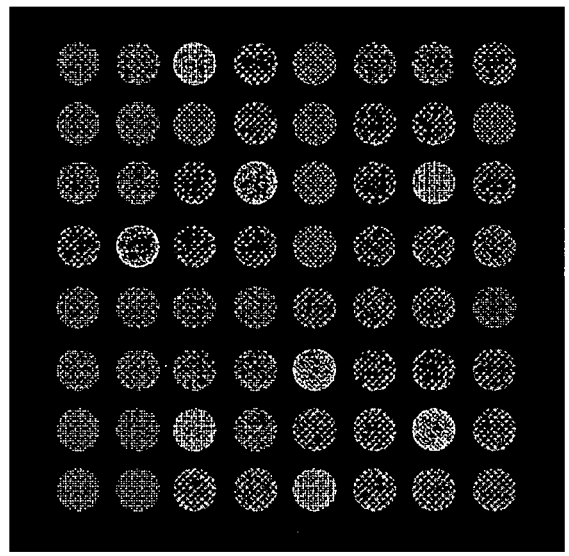
Figure 1D:
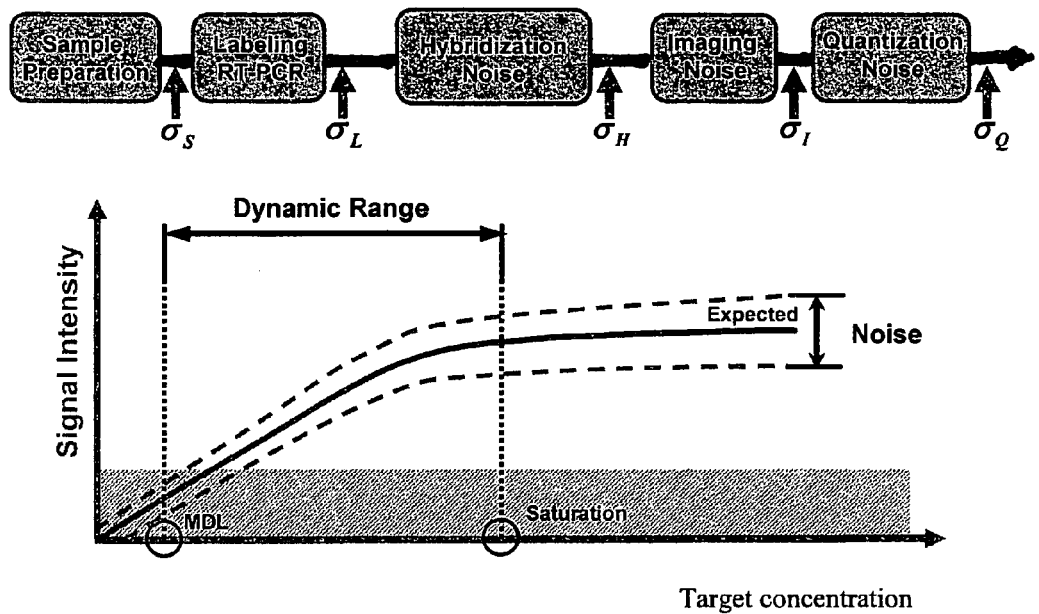
Figure 1E:
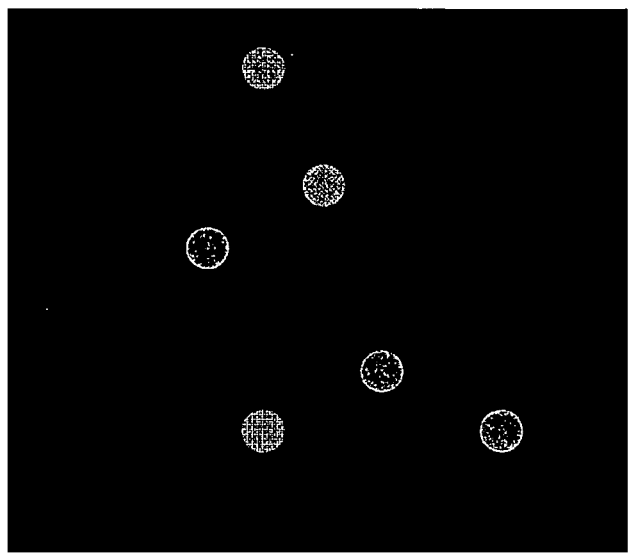

As used herein and in the appended claims, the singular forms "a," "and," and "the" include plural referents unless the context clearly dictates otherwise. Thus, for example, reference to "a microarray" includes a plurality of such microarrays and reference to "the nucleic acid" includes reference to one or more nucleic acids known to those skilled in the art, and so forth.

Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, devices and materials are described herein.

The publications discussed above and throughout the text are provided solely for their disclosure prior to the filing date of the present application. Nothing herein is to be construed as an admission that the inventors are not entitled to antedate such disclosure by virtue of prior disclosure.

DNA microarrays, which are, essentially, massively parallel affinity-based biosensors, are primarily used to measure gene expression levels, i.e., to quantify the process of transcription of DNA data into messenger RNA molecules (mRNA). The information transcribed into mRNA is further translated to proteins, the molecules that perform most of the functions in cells. Therefore, by measuring gene expression levels, researchers may be able to infer critical information about functionality of the cells or the whole organism. Accordingly, a perturbation from the typical expression levels is often an indication of a disease; thus DNA microarray experiments may provide valuable insight into the genetic causes of diseases. Indeed, one of the ultimate goals of DNA microarray technology is to allow development of molecular diagnostics and creation of personalized medicine.

A DNA microarray is basically an affinity-based biosensor where the binding is based on hybridization, a process in which complementary DNA strands specifically bind to each other creating structures in a lower energy state. Typically, the surface of a DNA microarray consists of an array (grid) of spots, each containing single stranded DNA oligonucleotide capturing molecules as recognition elements, whose locations are fixed during the process of hybridization and detection. Each single-stranded DNA capturing molecule typically has a length of 25-70 bases, depending on the exact platform and application. In the DNA microarray detection process, the mRNA that needs to be quantified is initially used to generate fluorescent labeled cDNA, which is applied to the microarray. Under appropriate experimental conditions (e.g., temperature and salt concentration), labeled cDNA molecules that are the perfect match to the microarray will hybridize, i.e., bind to the complementary capturing oligos. Nevertheless, there will always be a number of non-specific bindings since cDNA may non-specifically cross-hybridize to oligonucleotide that are not the perfect match but are rather only partial complements (having mismatches). Furthermore, the fluorescent intensities at each spot are measured to obtain an image, having correlation to the hybridization process, and thus the gene expression levels.

It is important to understand that this particular phenomenon, i.e., non-specific binding, is inherent to all affinity-based biosensors such as DNA or protein microarrays and is also inevitable, given that it originates from the probabilistic and quantum mechanical nature of molecular interactions and biochemical bonds present in these systems.

Currently, the sensitivity, dynamic range and resolution of all types of microarray data is limited by non-specific interactions (e.g., cross-hybridization in DNA microarrays), which may be interpreted as interference, in addition to several other sources of noise and systematic error in the detection procedure. The number of captured or labeled molecules varies due to the probabilistic nature of the binding or interactions. It has been observed that these variations are very similar to shot-noise (Poisson noise) at high analyte levels, yet more complex at low analyte levels where the interference (e.g., cross-hybridization) becomes the dominating limiting factor of the signal strength. Additionally, the measurements are also corrupted by the noise due to imperfect instrumentation and other biochemistry independent noise sources.

Typically, such non-specific interactions, such as cross-hybridization in DNA microarrays, are considered to be hurtful and often attempted to be suppressed by creating more specific probes. For instance, in the design of DNA microarrays, the capturing probes are often selected so that the sequences of nucleotides that comprise them are as unique as possible, and different from others as much as possible. Nevertheless, if the application requires distinguishing among similar targets, cross-hybridization is certainly present and perhaps limiting the accuracy. This may often be the fundamental limitation in microarrays designed for diagnostics and single nucleotide polymorphism (SNP) detection, for instance.

One of the main challenges for a precise detection and quantification is the correct identification and modeling of the noise sources, and the consecutive incorporation of the noise model in the design of optimal estimators. While the former has recently been experimentally studied, the latter is still largely unexplored.

A non-specific binding between unknown targets and known probes, as well as the shot-noise nature of the specific binding, are among the main obstacles for achieving high accuracy of measurements in microarray experiments. The invention utilizes statistical techniques to model the binding and design algorithms that detect the presence and estimate the quantities of the targets. The invention demonstrates that the accuracy of microarrays, independent of application, size of the array or detection method, can be improved to become noise-limited rather than interference-limited (e.g., cross-hybridization limited). This potentially increases the signal-to-noise ratio (SNR), dynamic range, and resolution of microarrays considerably; making them a significantly more quantitative and powerful tool in life-sciences research and medical diagnostics. The estimation technique of the invention is based on exploiting the stochastic nature of molecular binding, by utilizing a probabilistic model for specific binding as well as non-specific binding in affinity-based biosensors.

Today microarray platforms are very noisy, and exhibit a high-level of biochemical variation from experiment to experiment. To address this limitation, the underlying physics of noise in the whole microarray procedure from sample preparation to imaging which results in measurement uncertainties was analyzed.

In developing the solution in the context of DNA microarrays, the invention provides a process whereby (i) cross-hybridization is viewed as interference, rather than noise (akin to wireless communications interference, cross-hybridization actually has signal content); (ii) a model of hybridization and cross-hybridization as a stochastic processes; (iii) use of analytical methods (e.g., melting temperature or Gibbs free energy function) to construct models and use empirical data to fine tune the models; (iv) the detection and quantification of gene expression levels are viewed as a stochastic estimation problem; and (v) construction of optimal estimates. The invention uses statistical signal processing techniques to optimally detect and quantify the targets in microarrays by taking into account and exploiting the above uncertainties.

The invention provides methods, systems and computer programs on computer readable medium that model the hybridization and cross-hybridization processes by Markov chains, which suggests that these biosensors have a quantum-limited signal noise ratio (SNR) (Hassibi et al., J. Appl. Phys., 97:084701, 2005, incorporated herein by reference). Using the stationary distribution of the Markov chains, the invention provides methods to formulate a statistical model of microarray measurements.

In the methods of the invention, the biological noise is modeled as shot noise, thus accounting for the inherent fluctuations of the measured signal. Various criteria for the design of optimal algorithms for the detection of the presence and the estimation of the quantity of the target molecules were used. In some embodiments, the maximum-likelihood, maximum a posteriori, and constrained least-squares criteria were considered. Therefore, instead of trying to suppress the cross-hybridization, the invention essentially exploits it. This results in an increase in the signal to-interference-and noise ratio (SINR), and accordingly the precision of the microarray becomes limited by only the inherent noise, getting closer to its fundamental quantum-limited SNR.

Figure 1F:
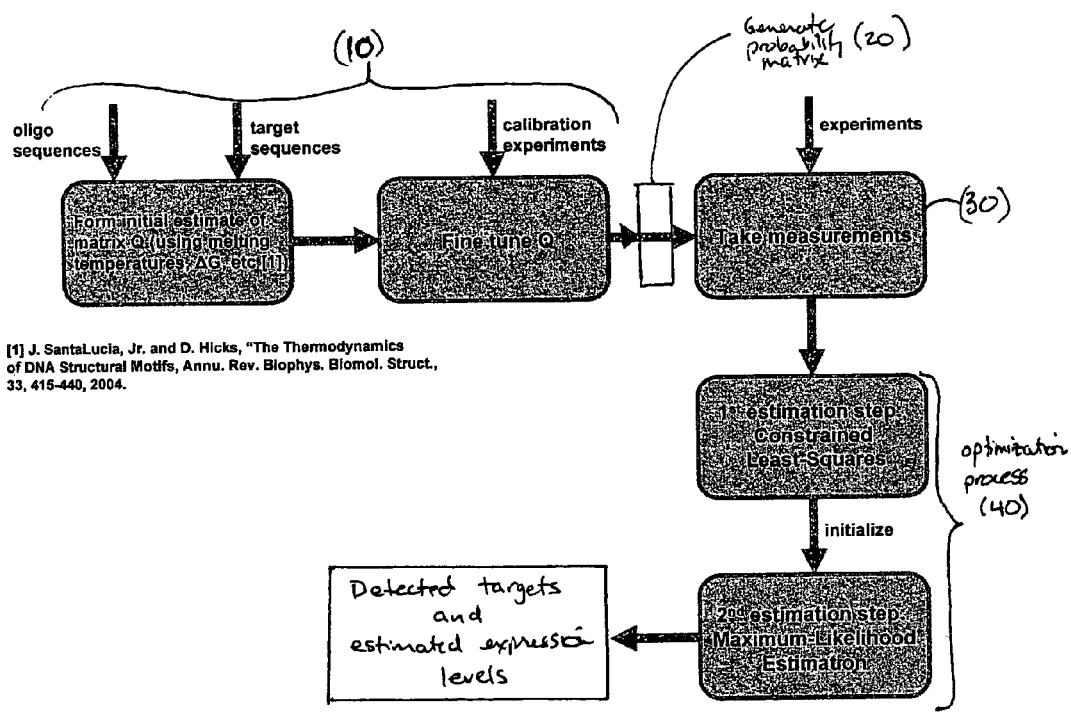

Referring to FIG. 1F there is shown a generalized method of the invention. The method can be implemented as further described herein below. FIG. 1F shows a flow diagram. The method comprises determining a theoretical estimate and/or an empirical estimate (10) of a probe and a target interaction in an array, this information is used to generate a probability matrix (20). Actual experimental data is then obtained (30) and modeled to the probability matrix (20). An optimization algorithm is then applied to exploit non-specific interactions (40).

In one aspect, the process of determining a theoretical estimate and/or and empirical estimate (10) comprises obtaining (i) analytical expression and (ii) calibration of the array using at least one standard probe. The analytical expression can comprise calculating a ΔG and/or a melting temperature and the calibration is by measuring the interaction of one or more targets and one or more probes.

Various optimization algorithms are known in the art that can be applied as in (40). For example, the optimization method can be selected from the group consisting of a maximum likelihood estimation algorithm, a maximum a-posteriori criterion, a constrained least squares calculation, and any combination thereof.

Figure 15A:
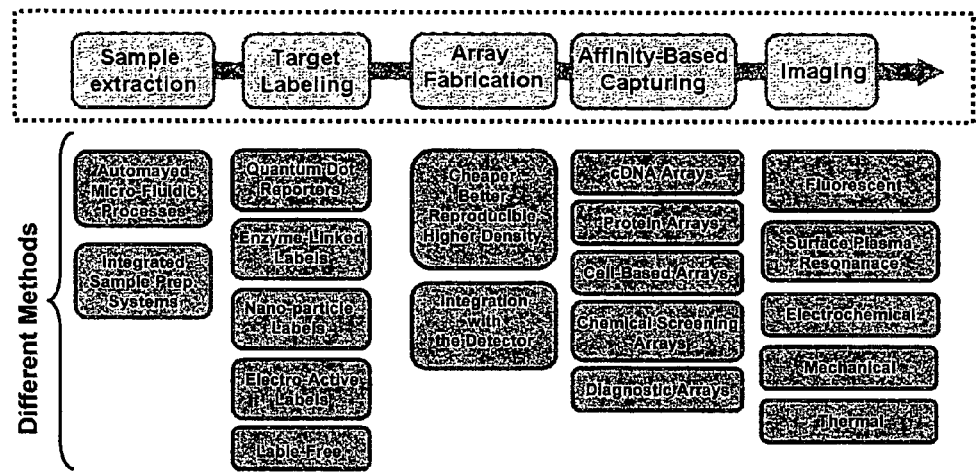
FIG. 15A-B show the various array applications that can be used with the methods and systems of the invention.
Figure 15B:
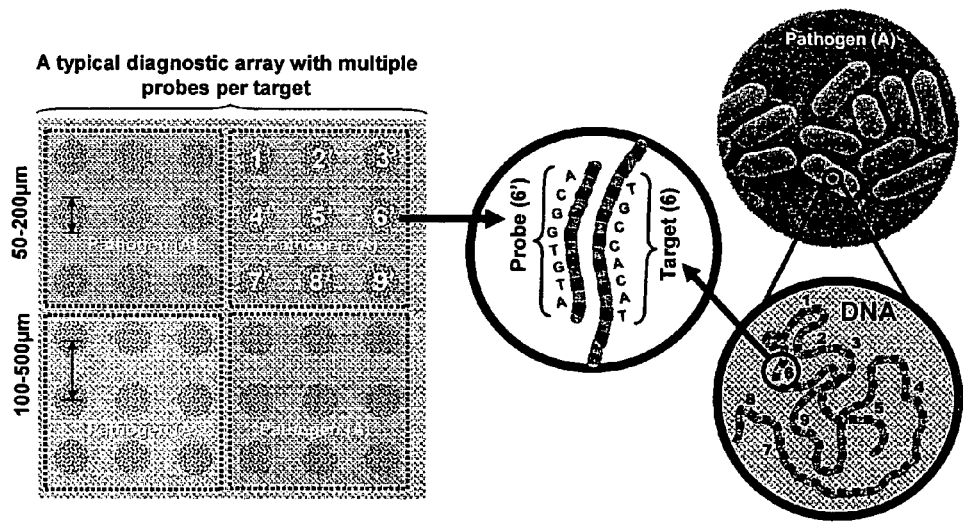

The methods and systems of the invention have application to a wide variety of array-based technologies (see, e.g., FIG. 15A-B). Various techniques and technologies may be used for synthesizing arrays of biological materials on or in a substrate or support. For example, a number of companies have developed methods for generating array and other microarray and polymer (including protein) array manufacturing methods and techniques. For example, a number of such techniques are described in U.S. patent Ser. No. 09/536,841, International Publication No. WO 00/58516; U.S. Pat. Nos. 5,143,854, 5,242,974, 5,252,743, 5,324,633, 5,445,934, 5,744,305, 5,384,261, 5,405,783, 5,424,186, 5,451,683, 5,482,867, 5,491,074, 5,527,681, 5,550,215, 5,571,639, 5,578,832, 5,593,839, 5,599,695, 5,624,711, 5,631,734, 5,795,716, 5,831,070, 5,837,832, 5,856,101, 5,858,659, 5,936,324, 5,968,740, 5,974,164, 5,981,185, 5,981,956, 6,025,601, 6,033,860, 6,040,193, 6,090,555, 6,136,269, 6,269,846, 6,022,963, 6,083,697, 6,291,183, 6,309,831 and 6,428,752; and in PCT Applications Nos. PCT/US99/00730 (International Publication No. WO 99/36760) and PCT/US01/04285, which are all incorporated herein by reference in their entireties for all purposes. Nucleic acid arrays are described in many of the above patents, but the same techniques generally may be applied to polypeptide arrays.

An array includes a collection of molecules (e.g., nucleic acids, polypeptides and the like) that can be prepared either synthetically or biosynthetically. The molecules may be the same (e.g., at least two are identical) or different in the array. The array may be in any number of structural formats.

A support or substrate used for preparation of an array include any material or group of materials having a rigid or semi-rigid surface or surfaces. In some embodiments, the support or substrate may take the form of beads, resins, gels, microspheres, or other materials and may be in any number of geometric configurations.

Targets used in microarrays refer to a molecule that recognizes a particular probe molecule on the substrate or support. A probe molecule will typically have an affinity for a given target. Probes may be naturally-occurring molecules or artificially synthesized molecules. The probes are processed so that, typically, they are spatially separated to allow proper association with a target. Targets are typically obtained from a biological sample to be tested.

The biological sample may be any sample suspected of containing a target that is capable of interacting with a probe molecule in the affinity-based array. For example, the sample may be a biological sample obtained from the environment or from a subject. Examples include a liquid, a gas, a tissue, blood, plasma, cerebrospinal fluid, urine and the like.

Probes may be attached, covalently or noncovalently, to a support or substrate, either directly or via a specific binding substance. Examples of targets that can be employed in accordance with this invention include, but are not limited to, antibodies, cell membrane receptors, antigens, drugs, oligonucleotides, nucleic acids, peptides, cofactors, lectins, sugars, polysaccharides, cells, cellular membranes, and organelles. Typically, a "probe-target pair" is formed when two macromolecules have combined through a molecular interaction or recognition to form a complex.

In some embodiments of the invention, the probe comprises nucleic acids. In other embodiments the probe can comprise amino acids. For example, the amino acids can be L-amino acids, D-amino acids, or synthetic amino acids. The nucleic acids can be, for example, any polymer or oligomer of nucleosides or nucleotides (polynucleotides or oligonucleotides) that include pyrimidine and/or purine bases, such as cytosine, thymine, and uracil, and adenine and guanine, respectively. Probes can comprise oligonucleotides or polynucleotides of deoxyribonucleic acid (DNA) or ribonucleic acid (RNA), which may be isolated from natural sources, recombinantly produced or artificially synthesized and mimetics thereof. Also included are peptide nucleic acid (PNA) in which the constituent bases are joined by peptides bonds rather than phosphodiester linkage, as described in Nielsen et al., Science 254:1497-1500 (1991); Nielsen, Curr. Opin. Biotechnol., 10:71-75 (1999), both of which are hereby incorporated by reference herein.

The term "nucleic acid" as used herein refers to a polymeric form of nucleotides of any length, either ribonucleotides, deoxyribonucleotides or peptide nucleic acids (PNAs), that comprise purine and pyrimidine bases, or other natural, chemically or biochemically modified, non-natural, or derivatized nucleotide bases. The backbone of the polynucleotide can comprise sugars and phosphate groups, as may typically be found in RNA or DNA, or modified or substituted sugar or phosphate groups. A polynucleotide may comprise modified nucleotides, such as methylated nucleotides and nucleotide analogs. Thus, the terms nucleoside, nucleotide, deoxynucleoside and deoxynucleotide generally include analogs such as those described herein. Nucleic acid arrays that are useful in the invention include those that are commercially available from Affymetrix, Inc. of Santa Clara, Calif.

In some embodiments, a probe is surface immobilized. Examples of probes that can be investigated in accordance with this invention include, but are not limited to, agonists and antagonists for cell membrane receptors, toxins and venoms, viral epitopes, hormones (e.g., opioid peptides, steroids, and like), hormone receptors, peptides, enzymes, enzyme substrates, cofactors, drugs, lectins, sugars, oligonucleotides, nucleic acids, oligosaccharides, proteins, and monoclonal antibodies.

Where the probe and target are nucleic acids, probes hybridize with targets having sufficient complementarity under appropriate conditions and remain at the probe location(s), while non-hybridized targets are washed away. These hybridized probe-target complexes, with their tags or labels, are thus spatially defined. The term "hybridization" refers to the process in which two single-stranded nucleic acid molecules bind non-covalently to form a stable double-stranded nucleic acid molecule. The term "hybridization" may also refer to triple-stranded hybridization, which is theoretically possible. Hybridization probes usually are nucleic acids (such as oligonucleotides) capable of binding in a base-specific manner to a complementary strand of nucleic acid. Such targets include peptide nucleic acids, as described in Nielsen et al., Science 254:1497-1500 (1991) or Nielsen Curr. Opin. Biotechnol., 10:71-75 (1999) (both of which are hereby incorporated herein by reference), and other nucleic acid analogs and nucleic acid mimetics.

Detection of the target-probe complex can serve a variety of purposes, such as to determine whether a target nucleic acid has a nucleotide sequence identical to or different from a specific probe sequence. Other uses include gene expression monitoring and evaluation (see, e.g., U.S. Pat. No. 5,800,992 to Fodor, et al.; U.S. Pat. No. 6,040,138 to Lockhart, et al.; and International App. No. PCT/US98/15151, published as WO99/05323, to Balaban, et al.), genotyping (U.S. Pat. No. 5,856,092 to Dale, et al.), or other detection of nucleic acids.

A scanner device is typically used to analyze arrays following contact with a sample comprising a probe. Various scanners are known in the art. The array may include targets of any type, as noted above. Labeled probes and/or targets may be detected using various commercial devices. In some aspect, the detection device (e.g., a scanner) images the target-probe complexes by detecting fluorescent or other emissions from the labels, or by detecting transmitted, reflected, or scattered radiation. Various detection schemes are employed depending on the type of emissions and other factors. A typical scheme employs optical and other elements to provide excitation light and to selectively collect the reflected or emitted light. Also included in some aspects are various light-detector systems employing photodiodes, charge-coupled devices, photomultiplier tubes, or similar devices to register the collected reflected or emitted light. In some embodiments of the invention, the scanner or sensing device is able to detect intrinsic characteristics of the target-probe complexes. Examples are arrays of electro-analytical transducers or mechanical transducers (see, e.g., A. Hassibi et al. ISSCC, 2005; and U.S. Patent Publication 2005000623, both of which are incorporated herein by reference).

The detection device (e.g., a scanner) provides data representing the intensities (and possibly other characteristics, such as color) of the detected reflected or emitted light, as well as the locations on the substrate where the emissions were detected. The data can be stored in memory, in the form of a data file or other data storage form or format. When displayed as an image for viewing or processing, picture elements, or pixels, represent this information. A pixel may have a single value representing the intensity of the elemental sub-area of the substrate from which the emissions were scanned. The pixel may also have another value representing another characteristic, such as color. Furthermore, the image may be converted from a first color space (e.g., RGB) to a second color space (e.g., HIS) prior to or during processing using algorithms of the invention.

For example, an image may comprise a plurality of pixels, the image may be represented by one or more pixels having high value(s) (e.g., a "bright" pixel), and one or more pixels of low value (e.g., a "dim" pixel). Alternatively, the chromatic value of a pixel may be made to represent the intensity, color, or other characteristic of the detected emissions.

Array images can be acquired and automated analysis can occur. In other aspect, the images may be acquired and a user may select a portion of the overall image to be analyzed by selecting the area in various ways known in the art through a user interface. Typically, the image data is provided in an automated, quantifiable, and repeatable way that is compatible with various image processing and/or analysis techniques. For example, the information may be provided for processing by a computer application that associates the locations where hybridized probes were detected with known locations where targets of known identities were synthesized or deposited.

The invention provides methods and computer programs for analyzing detected light or emissions. The invention can use various computer program products and software. In one aspect, a computer software application is used to process the image data of an array using the methods of the invention.

The various techniques, methods, and aspects of the invention described above can be implemented in part or in whole using computer-based systems and methods. Additionally, computer-based systems and methods can be used to augment or enhance the functionality described above, increase the speed at which the functions can be performed, and provide additional features and aspects as a part of or in addition to those of the invention described elsewhere in this document. Various computer-based systems, methods and implementations in accordance with the above-described technology are presented below.

A processor-based system can include a main memory, preferably random access memory (RAM), and can also include a secondary memory. The secondary memory can include, for example, a hard disk drive and/or a removable storage drive, representing a floppy disk drive, a magnetic tape drive, an optical disk drive, etc. The removable storage drive reads from and/or writes to a removable storage medium. Removable storage medium refers to a floppy disk, magnetic tape, optical disk, and the like, which is read by and written to by a removable storage drive. As will be appreciated, the removable storage medium can comprise computer software and/or data.

In alternative embodiments, the secondary memory may include other similar means for allowing computer programs or other instructions to be loaded into a computer system. Such means can include, for example, a removable storage unit and an interface. Examples of such can include a program cartridge and cartridge interface (such as the found in video game devices), a movable memory chip (such as an EPROM or PROM) and associated socket, and other removable storage units and interfaces, which allow software and data to be transferred from the removable storage unit to the computer system.

The computer system can also include a communications interface. Communications interfaces allow software and data to be transferred between computer system and external devices. Examples of communications interfaces can include a modem, a network interface (such as, for example, an Ethernet card), a communications port, a PCMCIA slot and card, and the like. Software and data transferred via a communications interface are in the form of signals, which can be electronic, electromagnetic, optical or other signals capable of being received by a communications interface. These signals are provided to communications interface via a channel capable of carrying signals and can be implemented using a wireless medium, wire or cable, fiber optics or other communications medium. Some examples of a channel can include a phone line, a cellular phone link, an RF link, a network interface, and other communications channels.

In this document, the terms "computer program medium" and "computer usable medium" are used to refer generally to media such as a removable storage device, a disk capable of installation in a disk drive, and signals on a channel. These computer program products are means for providing software or program instructions to a computer system.

Computer programs (also called computer control logic) are stored in main memory and/or secondary memory. Computer programs can also be received via a communications interface. Such computer programs, when executed, enable the computer system to perform the features of the invention as discussed herein. In particular, the computer programs, when executed, enable the processor to perform the features of the invention. Accordingly, such computer programs represent controllers of the computer system.

In an embodiment where the elements are implemented using software, the software may be stored in, or transmitted via, a computer program product and loaded into a computer system using a removable storage drive, hard drive or communications interface. The control logic (software), when executed by the processor, causes the processor to perform the functions of the invention as described herein.

In another embodiment, the elements are implemented primarily in hardware using, for example, hardware components such as PALs, application specific integrated circuits (ASICs) or other hardware components. Implementation of a hardware state machine so as to perform the functions described herein will be apparent to person skilled in the relevant art(s). In yet another embodiment, elements are implanted using a combination of both hardware and software.

In another embodiment, the computer-based methods can be accessed or implemented over the World Wide Web by providing access via a Web Page to the methods of the invention. Accordingly, the Web Page is identified by a Universal Resource Locator (URL). The URL denotes both the server machine and the particular file or page on that machine. In this embodiment, it is envisioned that a consumer or client computer system interacts with a browser to select a particular URL, which in turn causes the browser to send a request for that URL or page to the server identified in the URL. Typically the server responds to the request by retrieving the requested page and transmitting the data for that page back to the requesting client computer system (the client/server interaction is typically performed in accordance with the hypertext transport protocol ("HTTP")). The selected page is then displayed to the user on the client's display screen. The client may then cause the server containing a computer program of the invention to launch an application to, for example, perform an analysis according to the invention.

The working examples provided below are to illustrate, not limit, the disclosure. Various parameters of the scientific methods employed in these examples are described in detail below and provide guidance for practicing the disclosure in general.

EXAMPLES

An m×m DNA microarray, with $M \leq m^2$ different types of oligonucleotide targets attached to its surface was used. In other words, a particular oligonucleotide target may be present at more than one spot of the array. Each target is particularly designed to capture one of the possible probes in the sample that is required to be detected and quantified. Assuming a total of n molecules of N different types of cDNA probles, $N \leq M$, each consisting of $c_1, c_2, \ldots, c_N$ molecules ($\Sigma_{i=1}^{N} c_i = n$), are present in the sample that is applied to the microarray in the hybridization phase. For any target, there may be more than one spot on the m×m array where the complementary probes are located; the number of spots with probes that are complements to the target of the type i is denoted by $M_i$, and note that $$\sum_{i=1}^{M} M_i = m^2.$$

The array is scanned after the system has reached biochemical equilibrium. The resulting image has information about the number of targets captured at each spot and the goal is to detect which targets are present and to estimate their unknown concentrations $c_i$.

In general, in addition to hybridization to its matching oligonucleotide target, each probe molecule of type i may also engage in non-specific cross-hybridization with targets whose nucleotide sequences are only partial matches with the probe. In particular, for each target i, $k_i$ will denote the number of nonspecific cross-hybridizations. In the model, it is assumed that both hybridization and cross-hybridization are random events. Accordingly, let $p_i^h$ denote the probability that a probe of type i hybridizes to its matching target. If it is assumed that $p_i^H$ is the probability that probe i hybridizes to its matching target when it is in the proximity of its matching target then $$p_i^h = p_i^H \cdot \text{Prob (probe } i \text{ is in proximity of its matching gtarget)} = p_i^H \cdot \frac{1}{m^2},$$

where the fact that the probe molecules are undergoing a random walk to deduce the $$\frac{1}{m^2}$$

factor. The reason for expressing $p_i^h$ in terms of $p_i^H$ is that the latter is what depends on factors such as the chemistry and probe and target sequences. For example, $p_i^H$ can be estimated from the target and probe sequences, as well as the hybridization conditions, using the concepts of $\Delta G$ (Gibbs free energy change) and melting temperature.

Furthermore, let $p_{ij}^c$ denote the probability that a target of type i cross-hybridizes to a probe of type j. Similarly, we may write $$p_{ij}^c = \frac{p_{ij}^C}{m^2},$$

where $p_{ij}^C$ is the probability that target i cross-hybridizes with probe j when it is in its proximity. Cross-hybridization is not necessarily reciprocal: in other words, in general $p_{ij}^c \neq p_{ji}^c$. In fact, cross-hybridization need not even be mutual: if a target of type i cross-hybridizes to a probe of type j, the target j does not necessarily cross-hybridize to a probe of type i, i.e., it could be that $p_{ji}^c=0$ even though $p_{ij}^c>0$. Finally, the diffusion of the unbound target molecules is modeled as a random walk across the array. Thus, in equilibrium the distribution of the molecules is assumed to be uniform on the array.

If what exists is a probability of binding (i.e., hybridization and cross-hybridization) then, if enough probes are present, eventually all the target molecules would bind to the probes. However, this is not the case since both hybridization and cross-hybridization are reversible processes: once a target molecule is bound to a probe there is a nonzero probability that it will be released. The release probability for hybridization (i.e., the probability that target i is released from probe i) is denoted by $p_i^r$ and for cross-hybridization (i.e., the probability that target i is released from probe j) by $p_{ij}^r$. In this sense, any target molecule of type i can be in one of $k_i+2$ states: one state corresponding to hybridization to probe i, $k_i$ states corresponding to cross-hybridization to probes j, and one unbound state. The transition probabilities between these states are given by the probabilities $p_i^h$, $p_{ij}^c$, $p_i^r$ and $p_{ij}^r$. The corresponding Markov chain model is depicted in FIG. 1A for an example where $k_i=2$. The probability $$p_i^n = 1 - \Sigma_j p_{ij}^c - p_i^h$$

in FIG. 1 denotes the likelihood that an unbound target remains free.

An assumption that is made is that the probabilities $p_i^h$ and $p_{ij}^c$ are constant. In other words, they do not depend on the number of target molecules that are bound to different probes. It is certainly conceivable that if there are not enough probes, and/or if there are too many target molecules, then as more targets bind to probes there will be less probes available for binding and so the binding probabilities $p_i^h$ and $p_{ij}^c$ will decrease. This will essentially lead to saturation. Therefore in the model herein is restricted to the case where saturation is not met, i.e., assume that the concentration of target molecules relative to the number of probes is low. In addition, modeling the case where the binding probabilities $p_i^h$ and $p_{ij}^c$ are a function of the number of molecules already in a bounded state is quite interesting and possible and will allow one to study microarrays when the target concentrations are high.

Certain studies have shown that in some cases there can exist correlation or dependency between nearby probes on the chip (locational dependency). These have not been directly incorporated into the model, although in principle it is possible to do so by adjusting the values of the $p_i^h$ and $p_{ij}^c$ in accordance with the location of the probes. The calibration experiments which are used to fine tune the model do, in fact, make the corrections required by macroscopic issues such as the correlation between the nearby probes.

What the model addresses is the probability that a given molecule of type i is in any of the aforementioned $k_i+2$ states, once it has reached equilibrium. Let this be denoted by the probability vector $\mu_i=[\mu_{i,1} \mu_{i,2} \ldots \mu_{i,k_{i+2}}]^T$ where $\mu_{i,1}$ is the probability of being in the hybridized state, $\mu_{i,j}, 2 \leq j \leq k_{i+1}$ is the probability of being in the jth cross-hybridized state, and $\mu_{i,k_{i+2}}$ is the probability of being unbound. These probabilities are clearly given by the stationary distribution of the Markov chain, i.e., they satisfy:

$$\mu_i = P_i \mu_i, \mathbf{1}^T \mu_i = 1$$

where 1 denotes the vector of all 1's, and where the transition matrix $P_i$ is given by:

$$P_i = \begin{bmatrix} 1-p_i^r & 0 & \cdots & 0 & p_i^h \\ 0 & 1-p_{i1}^r & \cdots & 0 & p_{i1}^c \\ \vdots & \vdots & \ddots & \vdots & \vdots \\ 0 & 0 & \cdots & 1-p_{ik}^r & p_{ik}^c \\ p_i^r & p_{i1}^r & \cdots & p_{ik}^r & p_i^n \end{bmatrix}.$$

Since what is measured in a microarray is (an indication of) the number of molecules bound to any particular probe, let us now turn our attention from target molecules to probes. Thus, consider the $l^{th}$ probe, $l=1, 2, \ldots, m^2$ and let the number of target molecules of type i that are bound to it be given by $n_{li}$. The total number of molecules bound to probe l is given by $$n_{li} = \sum_{i=1}^{N} n_{li}.$$

Each $n_{li}$ is an independent binomial random variable, one of which corresponds to hybridization and the remaining to (possible) cross-hybridizations. Let us denote by $q_{li}$ the probability that a target of type i is bound to probe l. These can be readily found from the earlier computed $\mu_{ij}$s. In fact, $$q_{li} = \begin{cases} \mu_{i,1} & \text{if target } i \text{ hybridizes with probe } l \\ \mu_{i,j_i} & \text{if } l \text{ is the } j_i th \text{ probe target } i \text{ cross-hybridizes to } (2 \leq j_i \leq k_i) \\ 0 & \text{otherwise} \end{cases}$$

Since the total number of target molecules of type i that are available is given by $c_i$, the distribution of $n_{li}$ is given by:

$$p(n_{li}=x) = \binom{c_i}{x} q_{li}^x (1-q_{li})^{c_i-x} \quad (1)$$

Since the number of molecules involved is large, this is well approximated by a Gaussian random variable with the same mean $q_{li}c_i$ and variance $q_{li}(1-q_{li}2)c_i$. Furthermore, since the $n_{li}$ are independent, $n_l$ is well approximated by a Gaussian random variable with mean $$\sum_{i=1}^{N} q_{li} c_i$$

and variance $$\sum_{i=1}^{N} q_{li}(1-q_{li})c_i.$$

Arranging the $n_{li}$ into a $m^2 \times 1$ column vector $n=[n_1 n_2 \ldots n_{m^2}]^T$, the measurement obtained from a DNA microarray is $$s = n + v \quad (2)$$

where v is the noise due to imperfect instrumentation (e.g., read noise of scanner or camera) and other biochemistry independent noise sources and can be well modeled as having iid Gaussian entries with zero mean and variance $\sigma^2$. Recall further that n also can be represented as having independent Gaussian entries with mean $$\sum_{i=1}^{N} q_{li} c_i$$

and variance $$\sum_{i=1}^{N} q_{li}(1-q_{li})c_i.$$

Thus defining the N×1 column vector $$c = \frac{1}{m^2}[c_1 c_2 \ldots c_N]^T$$

we may write the microarray master equation:

$$s = Qc + w + v \qquad (3)$$

where Q is the matrix with (l, i) component $q_{li}$ and w is a zero-mean Gaussian random vector with covariance matrix $$E w w^T = \text{diag}\left(\sum_{i=1}^{N} q_{li}(1-q_{li})c_i, \ldots, \sum_{i=1}^{N} q_{m^2 i}(1-q_{m^2 i})c_i\right) \qquad (4)$$

The master equation (3) is the relationship between the measured signal s and the unknown target concentrations C. Note that once Q and $\sigma^2$ are given the model is fully specified. (Q can be obtained either by direct measurements or through knowledge of the probabilities $p_i^h$, $p_{ij}^c$, $p_i^r$, and $p_{ij}^r$.) Note also that the unknown concentrations (the $c_i$) are also present in the covariance matrix of w. In fact, this means that we have a shot noise model.

Below are a few criteria that may be used for recovering the unknown vector c in the microarray master equation (3). Furthermore, a lower bound (viz., the Cramer-Rao bound) is derived on the minimum mean-square error of the target concentrations estimation. In addition, this offers some discussions of the results.

The maximum-likelihood (ML) estimate of the input concentrations maximizes the probability $p_{s|c}(s|c)$, i.e., it is obtained by solving the optimization problem $$\max_{c \geq 0} p_{s|c}(s \mid c) \qquad (5)$$

where, due to Gaussian distribution of both w and v, yields $$p_{s|c}(s \mid c) = \frac{1}{(2\pi)^{M/2} \det(\Sigma_s)^{1/2}} e^{-\frac{1}{2}(s-Qc)^T \Sigma_s^{-1}(s-Qc)}$$

where the covariance matrix $\Sigma_s$ is given by $$\Sigma_s = \begin{bmatrix} \sigma^2 + \sum_{i=1}^{N} q_{1i}(1-q_{1i})c_i & \cdots & 0 \\ \vdots & \ddots & \vdots \\ 0 & \cdots & \sigma^2 + \sum_{i=1}^{N} q_{m^2 i}(1-q_{m^2 i})c_i \end{bmatrix}.$$

The optimization (5) is equivalent to the minimization $$\min_{c \geq 0}[(s-Qc) * \Sigma_s^{-1}(s-Qc) + \log \det \Sigma_s] \qquad (6)$$

Or $$\min_{c_i \geq 0} \sum_{l=1}^{m^2} \left[ \frac{\left(s_l - \sum_{i=1}^{N} q_{li} c_i\right)^2}{\sigma^2 + \sum_{i=1}^{N} q_{li}(1-q_{li})c_i} + \log\left(\sigma^2 + \sum_{i=1}^{N} q_{li}(1-q_{li})c_i\right) \right] \qquad (7)$$

Note that the above problem is highly nonlinear and non-convex. It can be solved via some iterative procedure. A good initial condition for any such iterative method can be found from the deterministic least-squares solution described further below.

In many cases one may have prior information about the target concentrations. In this case, one would want to use the maximum a-posteriori (MAP) estimate which maximizes $$p(c \mid s) = \frac{p(s \mid c) p(c)}{p(s)}$$

it is obtained by solving the optimization:

$$\max_{c \geq 0} p(s \mid c) p(c)$$

Here this reduces to:

$$\min_{c \geq 0}[(s-Qc) * \Sigma_s^{-1}(s-Qc) + \log \det \Sigma_s - \log p(c)] \qquad (8)$$

where $p(c) = p(c_1, \ldots, c_N)$ is the a priori information about the joint presence of the different targets. The a priori information in the MAP estimation therefore accommodates potential use of information obtained previously by some other means, i.e., it allows for biological data fusion.

The deterministic least-squares (LS) solution is obtained by solving the following optimization problem:

$$\min_{c \geq 0} \|s - Qc\|^2 \qquad (9)$$

Although this criterion does not have as nice a stochastic interpretation, it is a quadratic program that can be solved via efficient convex optimization techniques (e.g., the reflective Newton method). In other words, the inequality constraints $c_i \geq 0$ do not pose a problem. In fact, any other prior information (such as upper and lower bounds on the concentrations, saturation, etc.) that can be cast as inequality (or, more generally, convex) constraints can be readily incorporated into the method and solution.

As mentioned earlier, the solution obtained from deterministic least-squares is often a very good initial condition for iterative methods used for solving the ML and/or MAP problems.

The minimum mean-square error of any estimation procedure is lower bounded by the Cramer-Rao bound. One can compute and use this bound to characterize the limits of achievable performance of target quantification in microarrays.

Assuming an unbiased estimator, the Cramer-Rao lower bound (CRLB) on the minimum mean-square error of estimating a parameter $c_i$ is given by:

$$E(\hat{c}_i - c_i)^2 \geq [F^{-1}]_{ii} \tag{10}$$

where the Fisher information matrix F is given by the negative of the expected value of the Hessian matrix of $\log p_{s|c}(s)$. In other words, the entries of F are given by:

$$F_{ij} = -E_s \frac{\partial^2}{\partial c_i \partial c_j} \log p_{s|c}(s) \tag{11}$$

Since the expectation is over only s, F (and hence the CRLB) is a function of c. It is further convenient to define the entries of the Hessian matrix H as $$H_{ij} = \frac{\partial^2}{\partial c_i \partial c_j} \log p_{s|c}(s)$$

Note that H is a function of both s and c.

In this model, the function whose second deriviative we desire is:

$$L(c) = \log(p_{s|c}(s \mid c)) = -\frac{1}{2}\log(2\pi) - \frac{1}{2}\log\det\Sigma_s - \frac{1}{2}(s - Qc)^T \Sigma_s^{-1}(s - Qc)$$

Rather than attempt to computer the Hessian by evaluating two consecutive derivatives, it is more convenient to do so by perturbing c around two of its components, say $c_i$ and $c_j$, and noting that to second order $$L(c + e_i \delta c_i + e_j \delta c_j) = \tag{12}$$

$$L(c) + [\delta c_i \ \delta c_j] \begin{bmatrix} \frac{\partial L(c)}{\partial c_i} \\ \frac{\partial L(c)}{\partial c_j} \end{bmatrix} + \frac{1}{2}[\delta c_i \ \delta c_j] \begin{bmatrix} H_{ii} & H_{ij} \\ H_{ji} & H_{jj} \end{bmatrix} \begin{bmatrix} \delta c_i \\ \delta c_j \end{bmatrix},$$

where $e_i$ and $e_j$ are the $i^{th}$ and $j^{th}$ unit vectors with ones in the $i^{th}$ and $j^{th}$ components, respectively, and zeros elsewhere. To determine the expansion (12), it is useful to write the covariance matrix $\Sigma_s$ as:

$$\Sigma_s = D_0 + \sum_{i=1}^N D_i c_i$$

where $D_0 = \sigma^2 I_{m^2}$, and where $$D_i = \begin{bmatrix} q_{1i}(1-q_{1i}) & & & \\ & q_{2i}(1-q_{2i}) & & \\ & & \ddots & \\ & & & q_{m^2 i}(1-q_{m^2 i}) \end{bmatrix}.$$

Furthermore, note that:

$$L(c + e_i \delta c_i + e_j \delta c_j) =$$

$$-\frac{1}{2}\log(2\pi) - \frac{1}{2}L_1(c + e_i \delta c_i + e_j \delta c_j) - \frac{1}{2}L_2(c + e_i \delta c_i + e_j \delta c_j)$$

where $$L_1(c + e_i \delta c_i + e_j \delta c_j) = \log\det(\Sigma_s + D_i \delta c_i + D_j \delta c_j)$$

and $$L_2(c + e_i \delta c_i + e_j \delta c_j) = (s - Qc - Qe_i \delta c_i - Qe_j \delta c_j)^T$$
$$(\Sigma_s + D_i \delta c_i + D_j \delta c_j)^{-1}(s - Qc - Qe_i \delta c_i - Qe_j \delta c_j)$$

To find the contribusion of $L_1$ to the Hessian:

$$\log\det(I + X) \approx trX - \frac{1}{2}trX^2 + o(X^2)$$

to write (13):

$$L_1(c + e_i \delta c_i + e_j \delta c_j) = \log\det\Sigma_s + \log\det(I + \Sigma_s^{-1} D_i \delta c_i + \Sigma_s^{-1} D_j \delta c_j)$$

$$\approx \log\det\Sigma_s + tr(\Sigma_s^{-1} D_i \delta c_i + \Sigma_s^{-1} D_j \delta c_j) -$$
$$\frac{1}{2}tr[\Sigma_s^{-1} D_i \Sigma_s^{-1} D_i (\delta c_i)^2 +$$
$$2\Sigma_s^{-1} D_i \Sigma_s^{-1} D_j \delta c_i \delta c_j + \Sigma_s^{-1} D_j \Sigma_s^{-1} D_j (\delta c_j)^2]$$

Comparing (13) and (12), it is clear that $$\frac{\partial^2 L_1(c)}{\partial c_i \partial c_j} = -\frac{1}{2} tr(\Sigma_s^{-1} D_i \Sigma_s^{-1} D_j) \tag{14}$$

To find the contribution of $L_2(c + e_i \partial c_i + e_j \partial c_j)$ to the Hessian H, we use:

$$(I+A)^{-1} \approx -A + A^2 = o(A^2),$$

to obtain $$(\Sigma_s + D_i \delta c_i + D_j \delta c_j)^{-1} = (I + \Sigma_s^{-1} D_i \delta c_i + \Sigma_s^{-1} D_j \delta c_j)^{-1} \Sigma_s^{-1}$$

$$\approx [I - \Sigma_s^{-1} D_i \delta c_i - \Sigma_s^{-1} D_j \delta c_j +$$
$$2\Sigma_s^{-1} D_i \Sigma_s^{-1} D_j \delta c_i \delta c_j +$$
$$\Sigma_s^{-1} D_i \Sigma_s^{-1} D_i (\delta c_i)^2 +$$
$$\Sigma_s^{-1} D_j \Sigma_s^{-1} D_j (\delta c_j)^2] \Sigma_s^{-1}.$$

Putting this back in the expression for $L_2(c + e_i \partial c_i + e_j \partial c_j)$, it is not too difficult to identify $$\frac{\partial L_2(c)}{\partial c_i \partial c_i} = (s - Qc)^T \Sigma_s^{-1} D_i \Sigma_s^{-1} D_j \Sigma_s^{-1}(s - Qc) + \tag{15}$$

$$(s - Qc)^T \Sigma_s^{-1} D_i Q e_j + e_i^T Q^T \Sigma_s^{-1} Q e_j.$$

Using $E_s(s-Qc)=0$ and $E_s(s-Qc)(s-Qc)^T = \Sigma_s$ to obtain the expectation of (15) and combining the result with (14) yields:

$$E_s \frac{\partial^2 L(c)}{\partial c_i \partial c_j} = -e_i^T Q^T \Sigma_s^{-1} Q e_j - \frac{1}{2} tr(\Sigma_s^{-1} D_i \Sigma_s^{-1} D_j).$$

The (i,j) entry of the Fisher information matrix is therefore given by:

$$F_{ij} = e_i^T Q^T \Sigma_S^{-1} Q e_j + \frac{1}{2} tr(\Sigma_S^{-1} D_i \Sigma_S^{-1} D_j).$$

Note that with the definition of the diagonal matrices $D_i$:

$$tr(\Sigma_S^{-1} D_i \Sigma_S^{-1} D_J) = \sum_{k=1}^{m^2} \frac{1}{\sigma_{s,k}} D_{i,k} \frac{1}{\sigma_{s,k}} D_{j,k}$$

$$= \sum_{k=1}^{m^2} \frac{q_{ki}(1-q_{ki})q_{kj}(1-q_{kj})}{\sigma_{s,k}^2}$$

which is readily identified as the (I,j) component of the matrix $$(Q - Q \cdot Q)^T \Sigma_s^{-2}(Q - Q \cdot Q),$$

where • represents the direct product, $(A \cdot B)_{ij} = (A)_{ij}(B)_{ij}$. Therefore:

$$F = Q^T \Sigma_S^{-1} Q + \frac{1}{2}(Q - Q \cdot Q)^T \Sigma_S^{-2}(Q - Q \cdot Q). \quad (16)$$

The end result therefore is:

$$E(\hat{c}_i - c_i)^2 \geq \left[\left(Q^T \Sigma_S^{-1} Q + \frac{1}{2}(Q - Q \cdot Q)^T \Sigma_S^{-2}(Q - Q \cdot Q)\right)^{-1}\right]_{ii}. \quad (17)$$

Note that, being unbiased, the maximum-likelihood estimate (7) achieves the Cramer-Rao bound in (17). In most current applications of microarrays, one assumes that $N = m^2$ and estimation is performed by direct readout. In this case it is easy to see that the mean-square-error of direct readout is given by:

$$E_S(s-c)(s-c)^T = (Q-I)cc^T(Q-I)^T + \Sigma_S. \quad (18)$$

Comparing (18) with (17) for a given system model and concentrations, provides a measure of the improvements of the techniques proposed in this application over the currently widely used methods that employ direct readout.

In current microarray technology a great deal of effort is put into the design of the probes (often using some time-consuming form of combinatorial optimization) in such a way so as to minimize the effect of cross-hybridization. In some important applications, such as SNP detection, the desired targets are inherently similar and so eliminating the effect of cross-hybridization may not be completely possible.

Moreover, using the algorithms described herein, it may be that cross-hybridization can be turned to one's advantage. Take, for simplicity, the extreme case where our sample has only a single target, i.e., N=1. If an array has been designed that has no cross-hybridization then, assuming the target present is the first target, it will only bind to probe site number one and not to any of the other sites. The Fisher matrix from (17) becomes:

$$F_{11}^{nc} = \frac{q_{11}^2}{\sigma^2 + q_{11}(1-q_{11})c_1} + \frac{1}{2} \cdot \frac{q_{11}^2(1-q_{11})^2}{(\sigma^2 + q_{11}(1-q_{11})c_1)^2}. \quad (19)$$

Assume that the array does have cross-hyridization, i.e., that target 1 can bind to probe k with probability $q_{ki}$. The Fisher matrix now becomes:

$$F_{11}^c = \sum_{k=1}^{m^2} \left[\frac{q_{k1}^2}{\sigma^2 + q_{k1}(1-q_{k1})c_1} + \frac{1}{2} \cdot \frac{q_{k1}^2(1-q_{k1})^2}{(\sigma^2 + q_{k1}(1-q_{k1})c_1)^2}\right]$$

$$= F_{11}^{nc} + \sum_{k=2}^{m^2} \left[\frac{q_{k1}^2}{\sigma^2 + q_{k1}(1-q_{k1})c_1} + \frac{1}{2} \cdot \frac{q_{k1}^2(1-q_{k1})^2}{(\sigma^2 + q_{k1}(1-q_{k1})c_1)^2}\right]$$

$$\rangle F_{11}^{nc}.$$

In other words, the existence of cross-hybridization improves the accuracy of the estimate of target 1.

Of course, as one increases the number of targets beyond N=1, one would expect the improvement in accuracy to diminish and, in fact, for large enough N for the accuracy to degrade compared to the case of no hybridization. However, for what value of N this transition occurs depends very much on the values of the parameters a $\sigma^2$ and Q, on the concentration of the targets $c_i$ and on the number of probes $m^2$.

To illustrate this, consider an artificial example where we have N targets that hybridize to their corresponding probes with probability $q_{ii} = q$ and that cross-hybridize to all other (m2-1) probes with probability $q_{ij} = \beta$, $i \neq j$. Furthermore assume that the concentration of all N targets are identical, i.e., $c_i = c$, for $i = 1, \ldots, N$.

With these parameters it is not difficult to see that:

$$\Sigma_S = \sigma_S I_m, \sigma_S = (\sigma^2 + q(1-q)c + (N-1)\beta(1-\beta)c)$$

and that:

$$F = \begin{bmatrix} a & b & \cdots & b \\ b & a & \ddots & \vdots \\ \vdots & \ddots & \ddots & b \\ b & \cdots & b & a \end{bmatrix} = (a-b)I_N + 1 \cdot b \cdot 1^T,$$

where $$a = \frac{q^2}{\sigma_S} + \frac{q^2(1-q)^2}{2\sigma_S^2} + (m^2-1)\left[\frac{\beta^2}{\sigma_S} + \frac{\beta^2(1-\beta)^2}{2\sigma_S^2}\right]$$

$$b = \frac{2q\beta}{\sigma_S} + \frac{q(1-q)\beta(1-\beta)}{\sigma_S^2} + (m^2-2)\left[\frac{\beta^2}{\sigma_S} + \frac{\beta^2(1-\beta)^2}{2\sigma_S^2}\right]$$

Now inverting a matrix of the form of F above is straightforward since:

$$F^{-1} = ((a-b)I_N + 1 \cdot b \cdot 1^T)^{-1}$$

$$= \frac{1}{a-b}I_N - \frac{1}{a-b} 1 \frac{1}{b^{-1} + \frac{1^T 1}{a-b}} 1^T \frac{1}{a-b}$$

$$= \frac{1}{a-b}\left[I_N - \frac{1 \cdot b \cdot 1^T}{a+(N-1)b}\right].$$

Therefore:

$$[F^{-1}]_{11} = \frac{1}{a-b} \cdot \frac{a+(N-2)b}{a+(N-1)b}.$$

Figure 2:
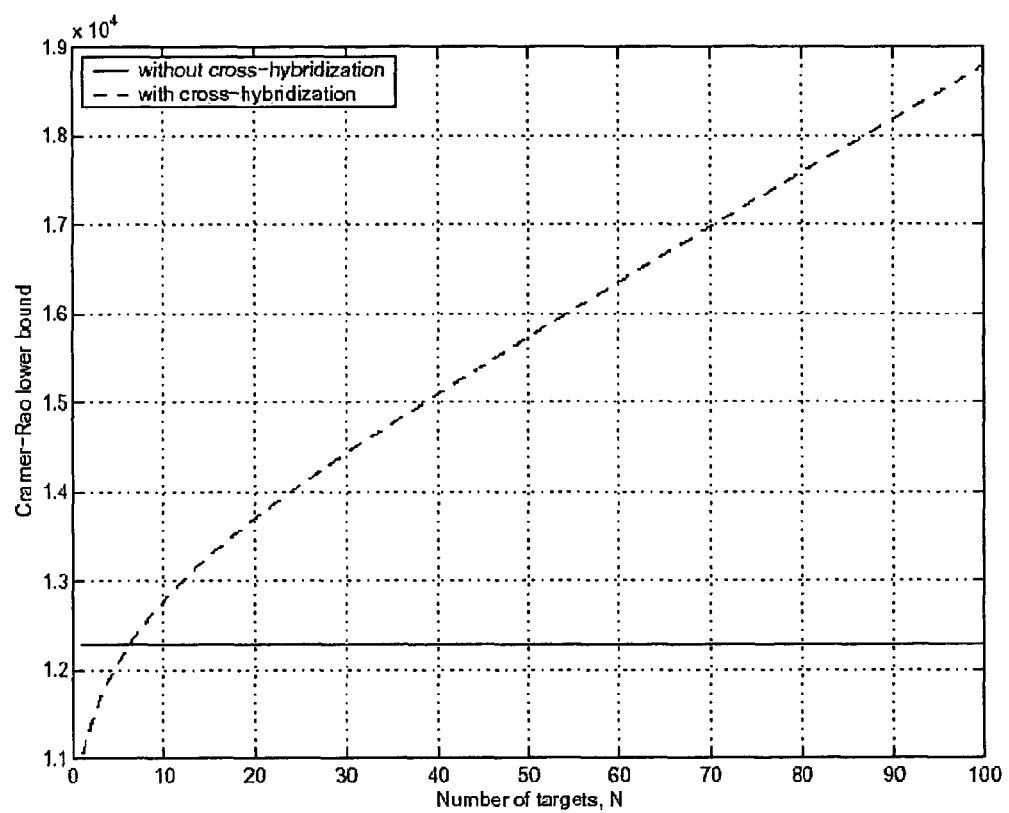
FIG. 2 shows the CRLB with and without cross-hybridization as a function of the number of target types N. The parameters are $\sigma^2=1000$, $c=500$, $m^2=100$ $q=0.3$ and $\beta=0.01$.

This is the CRLB that should be compared with the one without cross-hybridization in (19). FIG. 2 does this comparison for the parameters $\sigma^2=1000$, C=500, $M^2=100$ (i.e., a 10×10 array), q=0.3 and β=0.01. As can be seen from the figure, cross-hybridization is, in fact, beneficial when the number of targets is N≤6. Therefore the artificial example seem to indicate that there is benefit in having cross-hybridization in scenarios where the number of targets of interest in a given sample is much less than the number of probes on the array.

As set of experiments designed specifically to test the invention regarding the statistical model and to verify the performance of the estimation algorithms on the experimental data was performed as follows.

A set of oligonucleotide probes chosen from 96 genes of the bacterium *Escherichia coli* (specifically, the *E. coli* Array-Ready Oligo Set™ sample purchased from Operon Inc.); denote this set by:

$$P_{96} = \{P_1, P_2, \ldots, P_{96}\}$$

Each probe is a 70 mer and, even though the set is commercial and designed with minimization of cross hybridization in mind, there are many pairs of probes that are mutually similar. A subset of 10 such probes was selected, i.e., the probes are selected so that there is some cross-correlation between the sequences of nucleotides comprising them. The first probe was selected as $p_1=P_1$. To find the second probe, the sequence alignment functions in MATLAB's Bioinformatics Toolbox was used to find one that had significant cross-correlation with $p_1$. Call this probe $p_2$. In the process of determining $p_2$, two targets were also designed, $t_1$ and $t_2$, which are 25 mers such that they are Watson-Crick complements of certain subsequences of $p_1$ and $p_2$, respectively, and such that they have high cross-correlation with a certain subsequence of the other probe.

The process proceeded in a sequential manner by determining a probe, say $p_i$, that has significant cross-correlation with the probes selected earlier, $\{p_1, \ldots, p_{i-1}\}$ and in doing so designed a 25 mer target $t_i$ that hybribizes perfectly to $p_i$, yet has high cross-correlation with certain subsequences of the earlier probes $\{p_1, \ldots, p_{i-1}\}$.

At the end of the process a subset of 10 probes is obtained:

$$P_{10} = \{p_1, p_2, \ldots, p_{10}\}$$

As well as a set of 10 targets $$T_{10} = \{t_1, t_2, \ldots, t_{10}\}$$

The targets were highly purified and fluorescently labeled with Cy5 Cyanine dyes.

Two types of 10×10 arrays were designed: Type 1, which has all 96 probes from $P_{96}$,

| $P_1$ | $P_2$ | $P_3$ | $P_4$ | $P_5$ | $P_6$ | $P_7$ | $P_8$ | $P_9$ | $P_{10}$ |
|---|---|---|---|---|---|---|---|---|---|
| $P_{11}$ | $P_{12}$ | $P_{13}$ | $P_{14}$ | $P_{15}$ | $P_{16}$ | $P_{17}$ | $P_{18}$ | $P_{19}$ | $P_{20}$ |
| $P_{21}$ | $P_{22}$ | $P_{23}$ | $P_{24}$ | $P_{25}$ | $P_{26}$ | $P_{27}$ | $P_{28}$ | $P_{29}$ | $P_{30}$ |
| $P_{31}$ | $P_{32}$ | $P_{33}$ | $P_{34}$ | $P_{35}$ | $P_{36}$ | $P_{37}$ | $P_{38}$ | $P_{39}$ | $P_{40}$ |
| $P_{41}$ | $P_{42}$ | $P_{43}$ | $P_{44}$ | $P_{45}$ | $P_{46}$ | $P_{47}$ | $P_{48}$ | $P_{49}$ | $P_{50}$ |
| $P_{51}$ | $P_{52}$ | $P_{53}$ | $P_{54}$ | $P_{55}$ | $P_{56}$ | $P_{57}$ | $P_{58}$ | $P_{59}$ | $P_{60}$ |
| $P_{61}$ | $P_{62}$ | $P_{63}$ | $P_{64}$ | $P_{65}$ | $P_{66}$ | $P_{67}$ | $P_{68}$ | $P_{69}$ | $P_{70}$ |
| $P_{71}$ | $P_{72}$ | $P_{73}$ | $P_{74}$ | $P_{75}$ | $P_{76}$ | $P_{77}$ | $P_{78}$ | $P_{79}$ | $P_{80}$ |
| $P_{81}$ | $P_{82}$ | $P_{83}$ | $P_{84}$ | $P_{85}$ | $P_{86}$ | $P_{87}$ | $P_{88}$ | $P_{89}$ | $P_{90}$ |
| $P_{91}$ | $P_{92}$ | $P_{93}$ | $P_{94}$ | $P_{95}$ | $P_{96}$ | $P_1$ | $P_2$ | $P_3$ | $P_4$ |

Type 2, which contains only the probes from $P_{10}$,

| $p_1$ | $p_2$ | $p_3$ | $p_4$ | $p_5$ | $p_6$ | $p_7$ | $p_8$ | $p_9$ | $p_{10}$ |
|---|---|---|---|---|---|---|---|---|---|
| $p_{10}$ | $p_1$ | $p_2$ | $p_3$ | $p_4$ | $p_5$ | $p_6$ | $p_7$ | $p_8$ | $p_9$ |
| $p_9$ | $p_{10}$ | $p_1$ | $p_2$ | $p_3$ | $p_4$ | $p_5$ | $p_6$ | $p_7$ | $p_8$ |
| $p_8$ | $p_9$ | $p_{10}$ | $p_1$ | $p_2$ | $p_3$ | $p_4$ | $p_5$ | $p_6$ | $p_7$ |
| $p_7$ | $p_8$ | $p_9$ | $p_{10}$ | $p_1$ | $p_2$ | $p_3$ | $p_4$ | $p_5$ | $p_6$ |
| $p_6$ | $p_7$ | $p_8$ | $p_9$ | $p_{10}$ | $p_1$ | $p_2$ | $p_3$ | $p_4$ | $p_5$ |
| $p_5$ | $p_6$ | $p_7$ | $p_8$ | $p_9$ | $p_{10}$ | $p_1$ | $p_2$ | $p_3$ | $p_4$ |
| $p_4$ | $p_5$ | $p_6$ | $p_7$ | $p_8$ | $p_9$ | $p_{10}$ | $p_1$ | $p_2$ | $p_3$ |
| $p_3$ | $p_4$ | $p_5$ | $p_6$ | $p_7$ | $p_8$ | $p_9$ | $p_{10}$ | $p_1$ | $p_2$ |
| $p_2$ | $p_3$ | $p_4$ | $p_5$ | $p_6$ | $p_7$ | $p_8$ | $p_9$ | $p_{10}$ | $p_1$ |

To apply the estimation algorthims discussed herein, the matrix Q in (3) needed to be determined. To this end, the probabilities of hybridization and cross-hybridization of each of the 10 targets to any of the 10 probes are determined based on one or both of:
- analytical expression (e.g., ΔG, melting temperature, and the like);
- calibration experiments, where only 1 target is applied to a microarry, and its binding to each probes is quantified.

The melting temperature is used to get a rough estimate of the desired probabilities. Then the calibration experiments are used to fine-tune them. Two sets of calibration experiments were performed where the target quantity was 2 pmol in 50 microliters.

The final measurement obtained by the experiment is a 16-bit image (scanned by GenePix scanner by Axon Instrument) with the intensities of the pixels ranging between 0 and 65535. These intensities are correlated to the hybridization process. The results of the calibration experiments are summarized in the matrix R shown below.

$$R = kQ = \begin{bmatrix} 65 & 3 & 0 & 0 & 0 & 0 & 0 & 0 & 2 & 1 \\ 3 & 55 & 0 & 0 & 0 & 0 & 0 & 0 & 0 & 0 \\ 1 & 2 & 62 & 0 & 0 & 0 & 0 & 0 & 0 & 0 \\ 0 & 22 & 3 & 60 & 0 & 0 & 0 & 0 & 0 & 0 \\ 1 & 1 & 28 & 23 & 48 & 0 & 0 & 0 & 0 & 0 \\ 0 & 3 & 0 & 32 & 6 & 54 & 0 & 0 & 0 & 0 \\ 9 & 4 & 6 & 4 & 41 & 34 & 56 & 0 & 0 & 0 \\ 1 & 1 & 1 & 3 & 4 & 25 & 46 & 40 & 0 & 0 \\ 0 & 0 & 2 & 0 & 8 & 0 & 5 & 2 & 63 & 0 \\ 0 & 0 & 0 & 0 & 0 & 0 & 3 & 16 & 61 & 46 \end{bmatrix} \times 10^3.$$

The matrix R is proportional to the probability matrix Q whose (i,j) component is the probability that target j binds to probe i. The reason for having the factor k is that one does not directly measure the number of molecules (as suggested by (3)) but rather light intensity. Therefore k is essentially the factor that translates the concentration of target molecules to light intensity.

The peculiar (almost) lower-triangular structure of Q is an artifact of the sequential selection of the probes and targets in $P_{10}$ and $T_{10}$. Thus, $t_j$ is likely to cross-hybridize to probes selected earlier, i≤j, and not to ones selected later, i>j.

The performance of the estimation algorithm was tested in experiments where a mixture of 2 or 3 targets were applied to the designed microarrays. In particular, the mixtures $$T_1=\{t_2,t_4,t_7\},\ T_2=\{t_3,t_9\},\ T_3=\{t_5,t_6\}$$

were prepared, each with an equal amount of component target concentrations. The final concentrations of $T_1$, $T_2$, and $T_3$ were 1 pmol each, and were applied to a 50 microliter microarray reaction buffer. Each experiment was replicated four times. GenePix and MATLAB's Bioinformatics Toolbox were used for data analysis.

Figure 3:
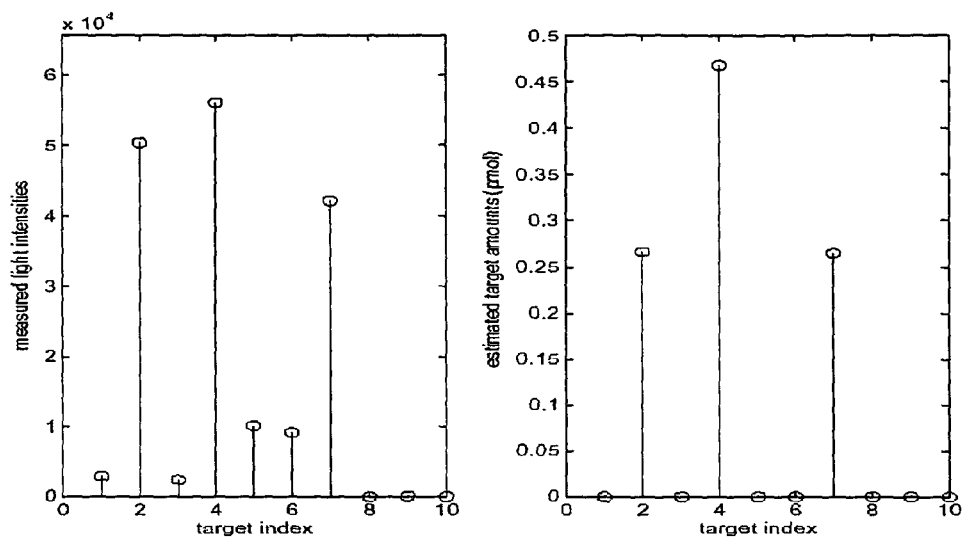
FIG. 3 shows the measured and estimated signal, $T_1$ mixture.
Figure 4:
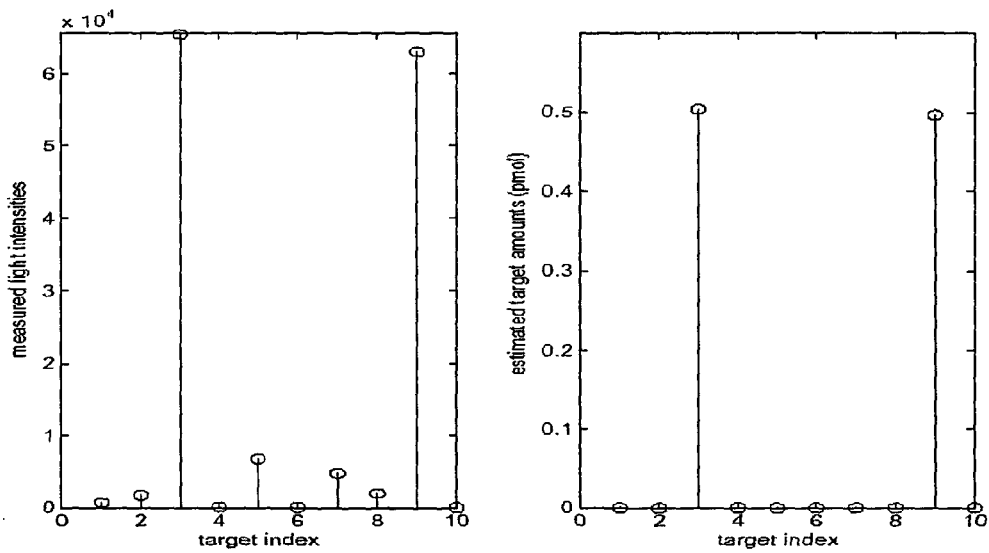
FIG. 4 is the measured and estimated signal, $T_2$ mixture.
Figure 5:
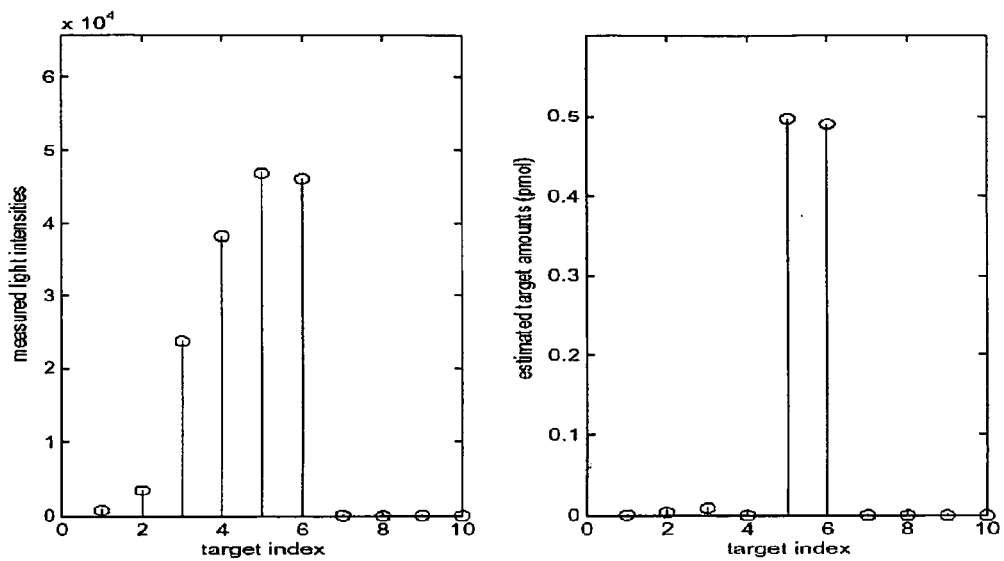
FIG. 5 is the measured and estimated signal, $T_3$ mixture.

FIGS. 3-5 show the measured signal and the estimated target quantities obtained from the constrained least-squares algorithm. FIG. 4 shows a very accurate estimation of the true target quantities of 50 pmol for targets $t_3$ and $t_9$. FIG. 3 shows a relatively good estimation of the target quantities of 33 pmol for targets $t_2$, $t_4$ and $t_7$. Note also that in both cases the artifacts due to cross-hybridization are suppressed, i.e., no target is incorrectly detected (as a false positive).

Figure 6:
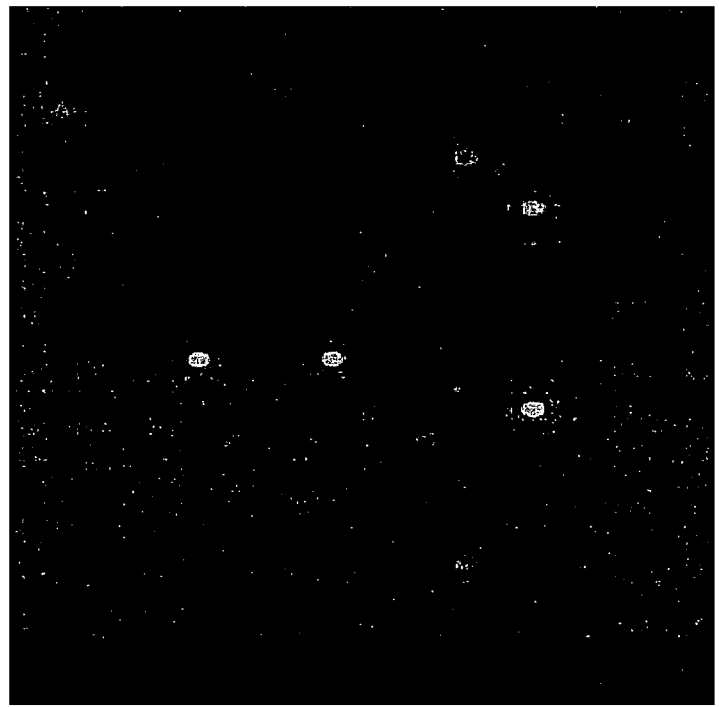
FIG. 6 shows the measured signal, $T_3$ applied to type 1 microarray.
Figure 7:
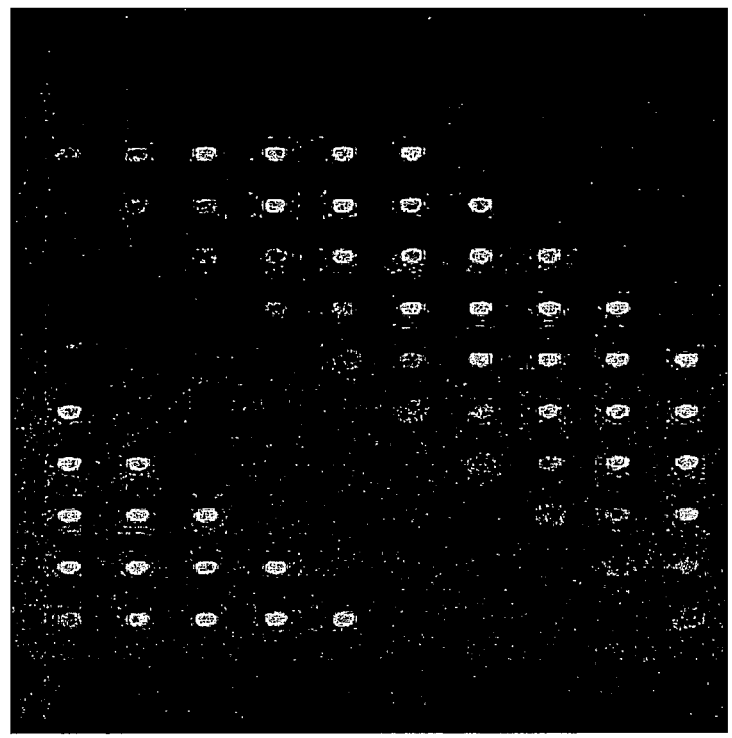
FIG. 7 shows the measured signal, $T_3$ applied to type 2 microarray.

A particularly interesting experiment is the one where $T_3$ is applied to the microarray. The signal that was measured is shown in FIG. 6 and FIG. 7 and indicates a significant presence of binding to not only targets $p_5$ and $P_6$, but also to $p_3$ and $p_4$. The raw measured data vector is $$[p_1,\ldots,p_{10}]=[800,3520,23760,38200,46820,46060,60,0,40,0]$$

However, from the design of the experiment the high levels of binding in spots 3 and 4 must be due to cross-hybridization since $T_3$ contains only targets $t_5$ and $t_6$. When the algorithm is applied to the measured data, it correctly identifies the presence of only 2 targets in the mixture, and quantifies them quite precisely as:

$$[t_1,\ldots,t_{10}]=[0,0,0,0,0.50,0.49,0,0,0,0]\ \text{pmol}.$$

The results of an experiment wherein the targets are actual *E. Coli* cDNA molecules in a rich biological background (typical of actual microarray experiments) is described below.

The targets used in the experiment are generated from The RNA Spikes™, a commercially available set of 8 purified RNA transcripts purchased from Ambion Inc. The sizes of the RNA sequences are (750; 752; 1000; 1000; 1034; 1250; 1475; 2000), respectively. These spikes are used for calibration purposes in microarrays and so have been chosen such that the eight sequences have minimal correlation. The RNA sequences were reverse transcribed to obtain cDNA targets, labeled with Cy5 dyes. Thirty-two probes (25 mer oligonucleotides) were designed, 4 for each of the 8 targets, and printed slides where each probe is repeated in 10 different spots (hence the slides have 320 spots). Denote the probes by $p_{ij}$, where $1\le i\le 8$; $1\le j\le 4$; therefore, $p_{ij}$ denotes the $j^{th}$ probe for the $i^{th}$ target. Furthermore, let $P_i=\{p_{ij}\}$, $1\le j\le 4$ be the probe set for target i. The probes are designed so that they cross-hybridize with one or more targets other than their intended ones.

The melting temperature is used to get a rough analytical estimate of the probabilistic model (i.e., of the matrix Q in the master equation (3)). Then calibration experiments were performed in order to fine-tune the model. Two sets of 8 calibration experiments were performed, wherein 2 ng of a single target was applied to a slide in every experiment. The experiments were done at T=24.8° C., the data was acquired with a GenePix scanner by Axon Instruments and analyzed with GenePixPro 6.0 and MATLAB's Bioinformatics Toolbox.

To test the performance of the estimation algorithm, a set of experiments was performed where a mixture of 3 targets was spiked with a complex biological background (from mouse total RNA). In particular, a mixture (r1, r2, r3)=(1, 0.75, 1.5) ng, and spiked it with 500 ng of the mouse RNA. The experiment was replicated four times. The conditions of these experiments were the same as the conditions of the calibration experiments.

Figure 8:
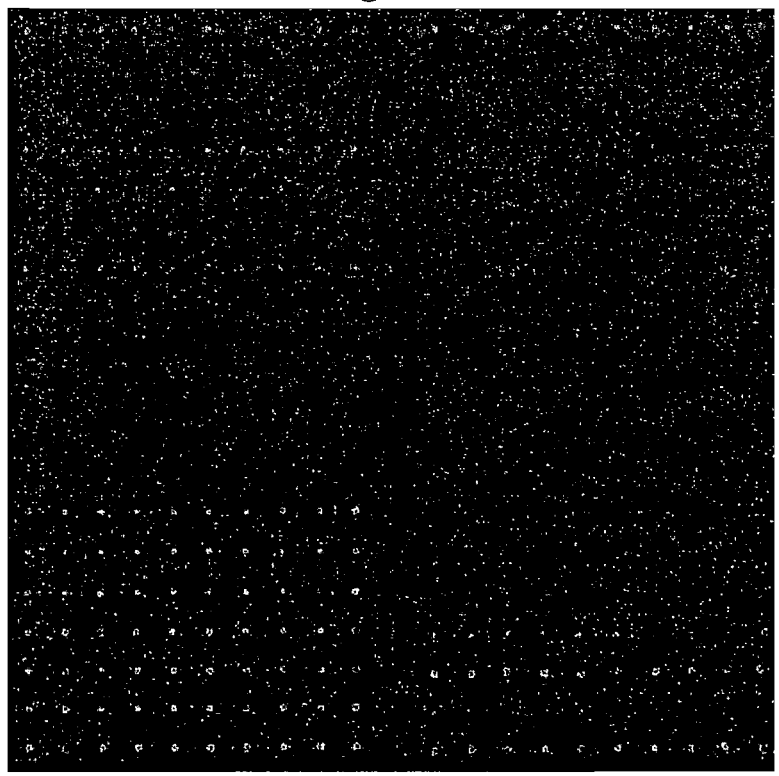
FIG. 8 shows the measured signal, $(r_1, r_2, r_3)=(1, 0.75, 1.5)$ ng of Ambion RNA spikes in 500 ng of mouse RNA background.
Figure 9:
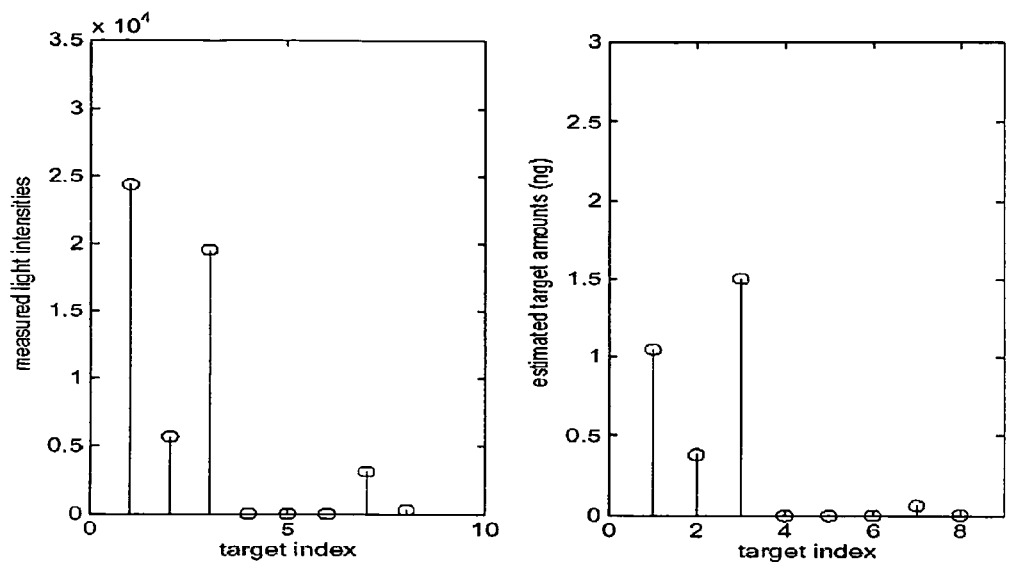
FIG. 9 shows the signal measured by the probes set $P_1$, and the corresponding target amount estimates.
Figure 10:
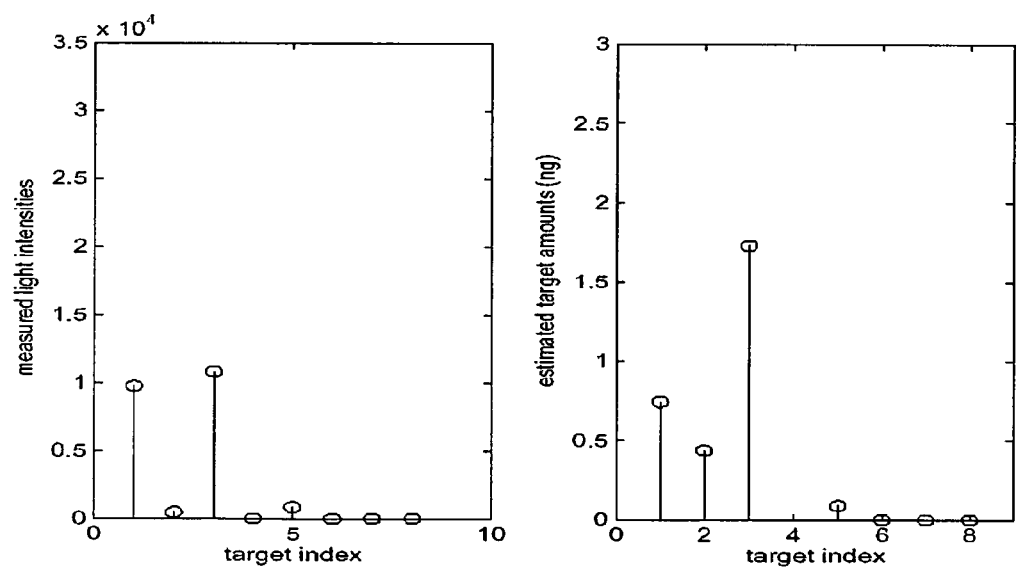
FIG. 10 shows signal measurements by the probe set $P_2$ and the corresponding target amount estimates.

FIG. 8 shows the scanned image. In FIG. 9, the measured signal and the estimated values of the targets using the probe set $P_1$ is shown. Similarly, FIGS. 10-12 show the measured signals and the estimated values of the targets using the probe sets $P_2$-$P_4$, respectively.

These figures show several interesting features. A direct readout of the signal obtained from FIG. 9 for probe set $P_1$ might lead an observer to conclude that there is more target $r_1$ than target $r_3$ in the applied mixture. However, the constrained least-squares algorithm corrects this, recovers the true relation of the targets in the mixture, and gives fairly accurate estimates of their quantities. It also suppresses the cross-hybridization artifact that may lead one to erroneously believe in the presence of $r_7$ in the mixture. Similar remarks apply to FIG. 10 (obtained from the probe set P2) where the algorithm correctly estimates the presence of target $r_2$, even though this barely evident from the direct readout.

Figure 11:
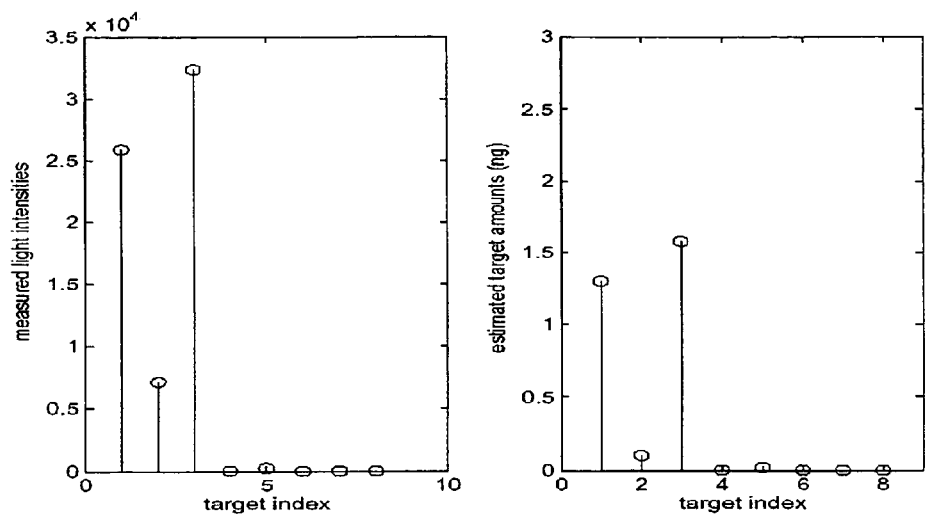
FIG. 11 shows signal measurements by the probe set $P_3$ and the corresponding target amount estimates.
Figure 12:
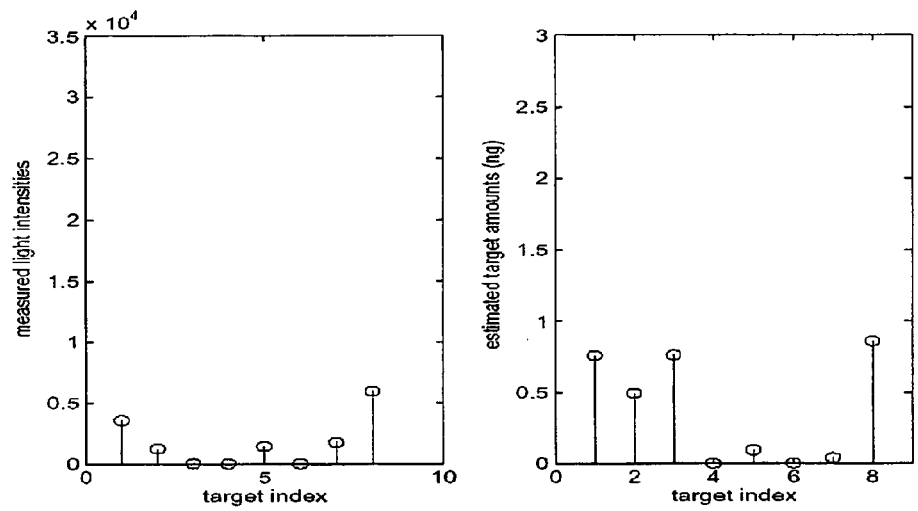
FIG. 12 shows signal measurements by the probe set $P_4$ and the corresponding target amount estimates.
Figure 13:
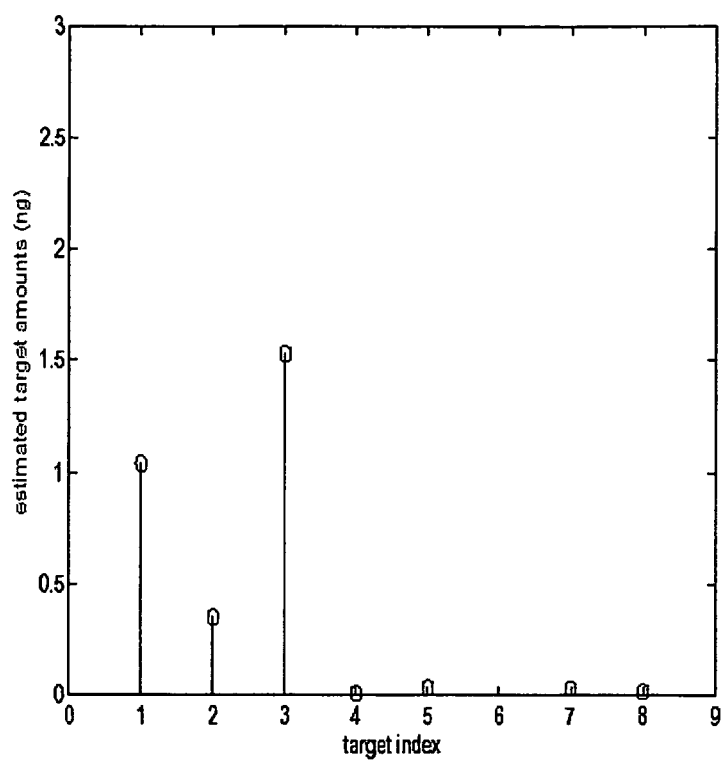
FIG. 13 shows target amounts estimated using all probes.
Figure 14:
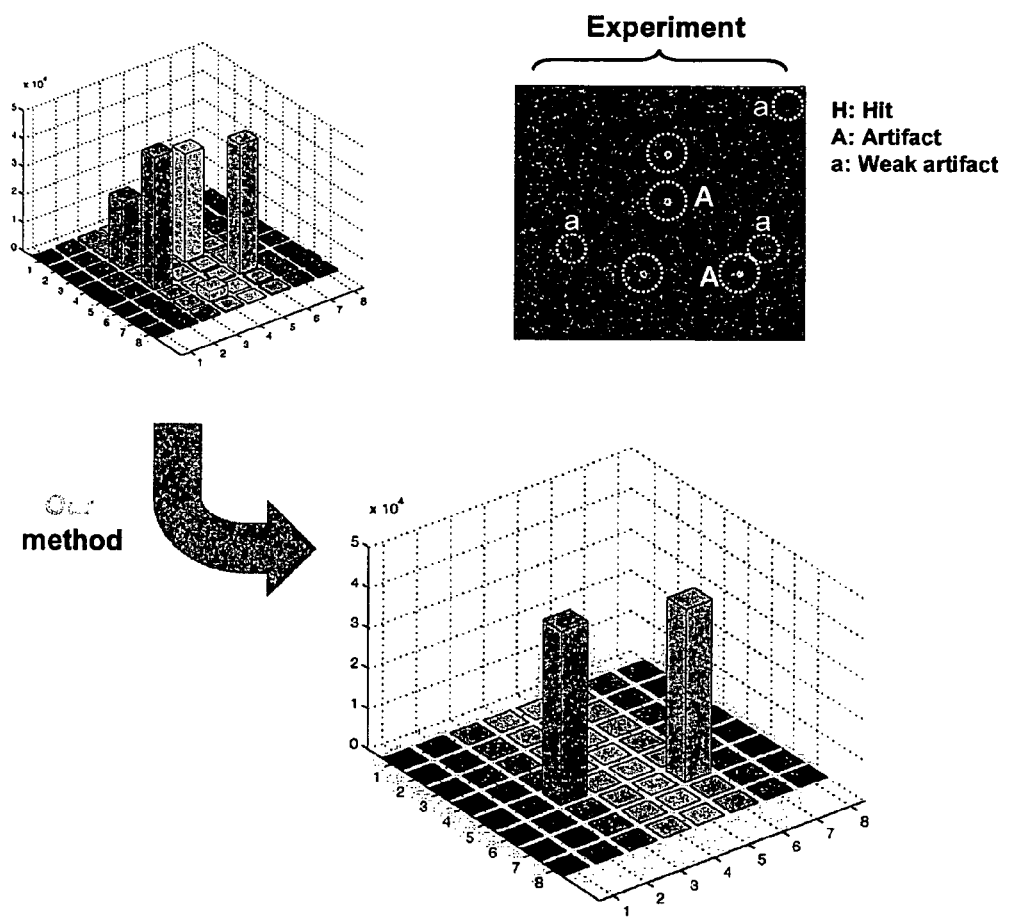
FIG. 14 shows the results of the use of a method and system of the invention. In a typical measurement in the absence of the disclosed invention, a direct readout suggests the presence of four targets, when in actuality there are only two. Using the methods and systems of the invention the number of true targets is identified as being two.

The presence of the biological background seems to most adversely affect the results of FIGS. 11 and 12 obtained from probe sets $P_3$ and $P_4$, respectively. In particular, in FIG. 12 the algorithm incorrectly identifies the presence of target $r_8$. However, when all four sets of probes are used for estimation, the targets are estimated quite precisely, as indicated by FIG. 13.

The results thus demonstrate that our algorithm is fairly robust with respect to the presence of rich biological background. Moreover, it should be surely possible to further improve the performance of the algorithm by incorporating the presence of a biological background into the statistical model.

The invention provides a statistical model for DNA microarrays based on a probabilistic description of the hybridization and cross-hybridization processes. In particular, when the target concentrations are not too high, or if the number of probes per site is not too low so that saturation does not occur a linear relationship is demonstrated between the unknown target concentrations and the measured light intensities. This linear relationship is perturbed by additive white Gaussian noise consisting of two components, one of which has a variance proportional to the number of targets (and hence is shot noise). The shot noise nature of the noise in DNA microarrays has been earlier observed experimentally.

The statistical model can be fully described by knowing the probability of different targets binding to different probes. Though these probabilities can be somewhat estimated based on the target and probe sequences, e.g., using the concepts of ΔG and melting temperature, it appears that one needs some sort of calibration experiments to estimate them more accurately.

The method is especially suited to low density arrays where the number of spots is not too large. There are many applications for such arrays in diagnostics, SNP detection, toxicology, and the like.

Once the probabilistic framework is in place, one may use a variety of statistical methods to estimate the target concentrations (e.g., ML, MAP, and constrained least-squares estimation). The invention also determined the Cramer-Rao bounds for estimation in DNA microarrays. The algorithm provided herein differs from current methods in that, rather than treating cross-hybridization as noise, it views it as interference and does estimation while taking it into account. In fact, some preliminary studies of the Cramer-Rao bounds suggest that cross-hybridization may, in fact, be beneficial. In particular, if a few target types are present in the sample (as is often the case in diagnostic applications), the existence of cross-hybridization can lead to more accurate estimates of the target concentrations, simply because there are more sites where the targets can bind, thus increasing the signal strength.

This result may have ramifications for probe design. [Currently, probe design is based on minimizing the amount of cross-hybridization.] Two sets of experiments were designed and performed, that confirmed the validity of the invention and the efficacy of the estimation techniques. The experiments included an example with a sample consisting of two oligonucleotide targets where existing techniques would detect the presence of four targets (the extra detected targets being an artifact of cross-hybridization). The algorithm, on the other hand, correctly detects only two targets and estimates their concentrations to remarkable accuracy.

Results of a similar flavor were obtained in experiments with cDNA targets in the presence of a complex biological background.

The work described herein can be extended in several ways. One is to generalize the model to the case where the target concentrations are high and saturation at the probes may occur. This would require modeling the probability of binding to different probes as a function of the number of targets that are already bound to the probes. Another direction would be to study ways to more accurately compute the probabilities of various targets and probes binding (including possible local dependencies). As mentioned earlier, this may allow the method to scale to high density arrays where extensive experimental calibration is not feasible. The methods of the invention are fairly robust to the presence of a complex biological background.

Although a number of embodiments and features have been described above, it will be understood by those skilled in the art that modifications and variations of the described embodiments and features may be made without departing from the teachings of the disclosure or the scope of the invention as defined by the appended claims.

What is claimed is:

1. A method of processing affinity-based array data, comprising:
    (a) determining an estimate of a probe and a target interaction in an array comprising (i) analytical expression and (ii) by calibration of the array using at least one standard probe;
    (b) generating a stochastic-matrix that utilizes the estimate in a Markov chain model that comprises modeling hybridization, cross-hybridization, and unbound transition probabilities between states;
    (c) obtaining optical affinity-based array data using a light detection device;
    (d) applying the array data to the stochastic-matrix;
    (e) applying an optimization algorithm selected from the group consisting of a maximum likelihood estimation algorithm, a maximum a-posteriori criterion, a constrained least squares calculation, and any combination thereof that exploits and does not suppress non-specific interactions by considering the non-specific interactions as interference rather than noise; and
    (f) outputting optimized affinity-based array data to a user, wherein the optimized affinity-based array data has an improved signal-to-noise ratio compared to the array data obtained by using the light detection device;
    wherein at least one of the steps (d)-(f) is executed by using a suitably programmed computer.

2. The method of claim 1, wherein the array is a nucleic acid array.

3. The method of claim 1, wherein the target is a nucleic acid.

4. The method of claim 1, wherein the probe is a nucleic acid.

5. The method of claim 1, wherein the analytical expression comprises calculating a $\Delta G$ and/or a melting temperature.

6. The method of claim 1, wherein the calibration is by measuring the interaction of one or more targets and one or more probes.

7. The method of claim 1, wherein the probe concentration is known and the optimization method comprises a maximum a-posteriori criterion.

8. The method of claim 1, wherein the combination comprises a constrained least squares calculation followed by a maximum likelihood estimation or a maximum a-posteriori criterion.

9. An automated microarray system of quantifying microarray data comprising:
    a light detector;
    a computer comprising means for converting light detected by using the light detector to data comprising a plurality of optical measured signals, the computer further comprising instructions for causing the data to be processed by the computer according to the method of claim 1.

10. A device for use in practicing the method of claim 1, the device comprising a signal detection element comprising a plurality of electrodes, wherein the electrodes are used to detect signal data caused by affinity-binding on an affinity binding array and a computer program medium selected from the group consisting of a removable storage device, a disk capable of installation in a disk drive, and signals on a channel, the medium tangibly embodying program instructions for quantifying the signal, the instructions operable for causing the apparatus to:
    determine an estimate of a probe and a target interaction in the affinity binding array comprising (i) analytical expression and (ii) by calibration of the array using at least one standard probe;
    generate a stochastic-matrix using the estimate in a Markov chain model that comprises modeling hybridization, cross-hybridization and unbound transition probabilities between states;
    apply signal data to the stochastic-matrix;
    apply an optimization algorithm selected from the group consisting of a maximum likelihood estimation algorithm, a maximum a-posteriori criterion, a constrained least squares calculation, and any combination thereof that exploits and does not suppress non-specific interactions by considering the non-specific interactions as interference rather than noise; and
    output specific binding data that depicts substantially accurate specific binding from the signal data.

11. The device of claim 10, wherein the device is an integrated device.

12. The device of claim 11, wherein the device has a chip configuration.

13. A computer program, residing on a computer program medium selected from the group consisting of a removable storage device, a disk capable of installation in a disk drive, and non-transitory signals on a channel, the medium comprising instructions for causing a computer to:

determine an estimate of a probe and a target interaction in an affinity-based array comprising (i) analytical expression and (ii) by calibration of the array using at least one standard probe;

generate a stochastic-matrix that utilizes the estimate in a Markov chain model that comprises modeling hybridization, cross-hybridization, and unbound transition probabilities between states;

obtain optical image affinity-based array data using a light detection device;

apply experimental optical image data to the stochastic-matrix;

apply an optimization algorithm selected from the group consisting of a maximum likelihood estimation algorithm, a maximum a-posteriori criterion, a constrained least squares calculation, and any combination thereof that exploits and does not suppress non-specific interactions by considering the non-specific interactions as interference rather than noise; and output specific binding data that depicts substantially accurate specific binding.

14. An apparatus comprising a light detection device that is used to obtain microarray image data from an array;

a computer-readable storage medium tangibly embodying program instructions for quantifying microarray image data, the instructions operable for causing the apparatus to:

determine an estimate of a probe and a target interaction in an array comprising (i) analytical expression and (ii) by calibration of the array using at least one standard probe;

generate a stochastic-matrix using the estimate in a Markov chain model that comprises modeling hybridization, cross-hybridization, and unbound transition probabilities between states;

apply experimental data comprising optical signal data of the microarray image data to the stochastic-matrix;

apply an optimization algorithm selected from the group consisting of a maximum likelihood estimation algorithm, a maximum a-posteriori criterion, a constrained least squares calculation, and any combination thereof that exploits and does not suppress non-specific interactions by considering the non-specific interactions as interference rather than noise; and output specific binding data that depicts substantially accurate specific binding from the microarray image data.

* * * * *